(12) United States Patent
Haase

(10) Patent No.: US 10,143,796 B2
(45) Date of Patent: Dec. 4, 2018

(54) FLUID DELIVERY DEVICE REFILL ACCESS

(75) Inventor: James M. Haase, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 1054 days.

(21) Appl. No.: 13/218,007

(22) Filed: Aug. 25, 2011

(65) Prior Publication Data

US 2012/0053562 A1 Mar. 1, 2012

Related U.S. Application Data

(60) Provisional application No. 61/376,827, filed on Aug. 25, 2010.

(51) Int. Cl.
*A61M 5/142* (2006.01)
*A61M 5/168* (2006.01)

(52) U.S. Cl.
CPC .... *A61M 5/14216* (2013.01); *A61M 5/14276* (2013.01); *A61M 5/168* (2013.01); *A61M 5/16813* (2013.01); *A61M 2209/045* (2013.01)

(58) Field of Classification Search
CPC ...... A61M 39/0208; A61M 2039/0211; A61M 2039/0226; A61M 2039/0244; A61M 2039/0241; A61M 39/04; A61M 2039/0223; A61M 2039/022; A61M 39/045; A61M 5/16827; A61M 2039/0081; A61M 2039/0217; A61M 2039/0238; A61M 2039/0063; A61M 2039/009; A61B 2019/462; A61B 17/3403; A61B 5/6865
USPC ........ 604/288.02, 288.01, 93.01, 288.04, 86, 604/288.03, 502, 116, 536, 201
See application file for complete search history.

(56) References Cited

U.S. PATENT DOCUMENTS

| | | | | |
|---|---|---|---|---|
| 2,911,123 | A * | 11/1959 | Saccomanno | 215/247 |
| 3,923,060 | A | 12/1975 | Ellinwood, Jr. | |
| 4,193,397 | A * | 3/1980 | Tucker et al. | 604/502 |
| 4,496,343 | A * | 1/1985 | Prosl et al. | 604/86 |
| 4,571,749 | A * | 2/1986 | Fischell | 600/31 |
| 4,573,994 | A * | 3/1986 | Fischell et al. | 604/891.1 |
| 4,604,090 | A * | 8/1986 | Reinicke | 604/118 |
| 4,710,174 | A * | 12/1987 | Moden et al. | 604/175 |

(Continued)

FOREIGN PATENT DOCUMENTS

| | | |
|---|---|---|
| WO | 9312825 A1 | 7/1993 |
| WO | 2005007223 A2 | 1/2005 |
| WO | 2010096449 A2 | 8/2010 |

OTHER PUBLICATIONS

U.S. Appl. No. 13/220,359, filed Aug. 29, 2011, Petri.

(Continued)

*Primary Examiner* — Kami A Bosworth
*Assistant Examiner* — William Carpenter
(74) *Attorney, Agent, or Firm* — Shumaker & Sieffert, P.A.

(57) ABSTRACT

A therapeutic fluid delivery system including, in various examples, a first reservoir configured to house a first therapeutic fluid, a second reservoir configured to house a second therapeutic fluid, and an inlet port configured to receive a fluid delivery needle is described. The inlet port is configured for fluid communication between the fluid delivery needle and the first reservoir, and the inlet port is further configured for fluid communication between the fluid delivery needle and the second reservoir.

39 Claims, 9 Drawing Sheets

(56) References Cited

U.S. PATENT DOCUMENTS

| | | | |
|---|---|---|---|
| 4,714,462 A | | 12/1987 | DiDomenico |
| 4,832,054 A | * | 5/1989 | Bark .............................. 128/899 |
| 4,955,861 A | * | 9/1990 | Enegren ............ A61M 5/14276 604/141 |
| 4,978,338 A | * | 12/1990 | Melsky et al. ............ 604/288.02 |
| 5,006,115 A | * | 4/1991 | McDonald ................... 604/175 |
| 5,226,879 A | * | 7/1993 | Ensminger et al. ..... 604/288.03 |
| 5,263,930 A | * | 11/1993 | Ensminger ............... 604/288.03 |
| 5,328,465 A | * | 7/1994 | Kratoska et al. ........ 604/288.02 |
| 5,336,194 A | * | 8/1994 | Polaschegg et al. ......... 604/175 |
| 5,395,324 A | | 3/1995 | Hinrichs et al. |
| 5,667,504 A | | 9/1997 | Baumann et al. |
| 5,695,490 A | * | 12/1997 | Flaherty et al. ........... 604/891.1 |
| 5,769,823 A | | 6/1998 | Otto |
| 5,814,019 A | | 9/1998 | Steinbach et al. |
| 5,820,589 A | | 10/1998 | Torgerson et al. |
| 6,190,352 B1 | * | 2/2001 | Haarala et al. ............ 604/93.01 |
| 6,293,922 B1 | | 9/2001 | Haase |
| 6,416,495 B1 | | 7/2002 | Kriesel et al. |
| 6,459,917 B1 | * | 10/2002 | Gowda et al. ................ 600/345 |
| 6,471,675 B1 | | 10/2002 | Rogers et al. |
| 6,554,822 B1 | | 4/2003 | Holschneider et al. |
| 6,764,472 B1 | * | 7/2004 | Burke et al. ............. 604/288.04 |
| 7,811,279 B2 | | 10/2010 | John |
| 7,914,499 B2 | | 3/2011 | Gonnelli et al. |
| 8,348,909 B2 | * | 1/2013 | Haase ............... A61M 5/14276 604/288.01 |
| 8,721,605 B2 | * | 5/2014 | Brandt et al. ............ 604/288.01 |
| 2001/0020471 A1 | | 9/2001 | Kitten |
| 2002/0156462 A1 | | 10/2002 | Stultz |
| 2003/0050623 A1 | | 3/2003 | Lord et al. |
| 2003/0133358 A1 | | 7/2003 | Karp |
| 2003/0176833 A1 | | 9/2003 | Libermann |
| 2004/0073196 A1 | * | 4/2004 | Adams ............... A61M 39/0208 604/890.1 |
| 2004/0143242 A1 | | 7/2004 | Ludin et al. |
| 2005/0070875 A1 | | 3/2005 | Kulessa |
| 2005/0113745 A1 | | 5/2005 | Stultz |
| 2005/0256451 A1 | * | 11/2005 | Adams et al. ............. 604/93.01 |
| 2005/0273083 A1 | | 12/2005 | Lebel et al. |
| 2006/0089619 A1 | * | 4/2006 | Ginggen ........... A61M 5/14276 604/891.1 |
| 2006/0142705 A1 | * | 6/2006 | Halili ....................... 604/288.01 |
| 2006/0270983 A1 | | 11/2006 | Lord et al. |
| 2006/0271021 A1 | | 11/2006 | Steinbach |
| 2006/0271022 A1 | | 11/2006 | Steinbach et al. |
| 2007/0197968 A1 | | 8/2007 | Pongpairochana |
| 2007/0255235 A1 | * | 11/2007 | Olsen et al. ............. 604/288.01 |
| 2007/0255237 A1 | * | 11/2007 | Lobl ................. A61M 5/14276 604/288.01 |
| 2007/0255261 A1 | * | 11/2007 | Haase ........................ 604/891.1 |
| 2008/0039820 A1 | * | 2/2008 | Sommers et al. ............ 604/539 |
| 2008/0060442 A1 | | 3/2008 | Smith |
| 2008/0243093 A1 | * | 10/2008 | Kalpin et al. ............ 604/288.02 |
| 2008/0287887 A1 | | 11/2008 | Mack et al. |
| 2009/0227989 A1 | | 9/2009 | Burke et al. |
| 2010/0089487 A1 | | 4/2010 | Burke et al. |
| 2010/0125246 A1 | * | 5/2010 | Kalpin ......................... 604/151 |
| 2010/0274196 A1 | | 10/2010 | Brandt et al. |
| 2011/0125137 A1 | | 5/2011 | Christenson |
| 2011/0166522 A1 | * | 7/2011 | Haase ............... A61M 39/0208 604/151 |
| 2011/0172633 A1 | | 7/2011 | Ali et al. |
| 2012/0053514 A1 | | 3/2012 | Robinson |
| 2012/0053571 A1 | | 3/2012 | Petri |

OTHER PUBLICATIONS

U.S. Appl. No. 13/217,981, filed Aug. 25, 2011, Robinson et al.
Response to Office Action dated Aug. 2, 2013, from U.S. Appl. No. 13/217,981, filed Nov. 4, 2013, 17 pages.
Office Action from U.S. Appl. No. 13/217,981, dated Aug. 2, 2013, 14 PP.
Final Office Action from U.S. Appl. No. 13/217,981, dated Feb. 28, 2014, 21 pp.
Response to Office Action dated Feb. 28, 2014, from U.S. Appl. No. 13/217,981, filed Apr. 24, 2014, 16 pp.
Response to Office Action dated Oct. 2, 2014, from U.S. Appl. No. 13/220,359, dated Dec. 23, 2014, 16 pp.
Office Action from U.S. Appl. No. 13/220,359, dated Oct. 2, 2014, 11 pp.
Office Action from U.S. Appl. No. 13/217,981, dated Feb. 25, 2015, 29 pp.
Final Office Action from U.S. Appl. No. 13/220,359, dated Feb. 26, 2016, 18 pp.
Office Action from U.S. Appl. No. 13/217,981 dated Apr. 8, 2016, 25 pp.
Final Office Action from U.S. Appl. No. 13/217,981, dated Nov. 5, 2015, 24 pp.
Response to Office Action dated Apr. 8, 2016, from U.S. Appl. No. 13/217,981, filed Jul. 8, 2016, 22pp.
Final Office Action from U.S. Appl. No. 13/217,981, dated Oct. 20, 2016, 26 pp.
Amendment in Response to Office Action dated Oct. 20, 2016, from U.S. Appl. No. 13/217,981, filed Jan. 19, 2017, 20 pp.
Notice of Allowance from U.S. Appl. No. 13/217,981, dated Apr. 11, 2017, 21 pp.

* cited by examiner

FLUID DELIVERY DEVICE REFILL ACCESS

This application claims the benefit of U.S. Provisional Application No. 61/376,827, filed Aug. 25, 2010, the entire content of which is incorporated herein by this reference.

TECHNICAL FIELD

This disclosure generally relates to implantable medical devices and, more particularly, to implantable fluid delivery devices.

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic fluids, such as drugs to patients. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device that can deliver a drug or other therapeutic fluid to a patient at a selected site. A drug infusion device may be partially or completely implanted at a location in the body of a patient and deliver a fluid medication through a catheter to a selected delivery site in the body. Drug infusion devices, such as implantable drug pumps, commonly include a reservoir for holding a supply of the therapeutic fluid, such as a drug, for delivery to a site in the patient. The fluid reservoir can be self-sealing and accessible through one or more ports. A pump is fluidly coupled to the reservoir for delivering the therapeutic fluid to the patient. A catheter provides a pathway for delivering the therapeutic fluid from the pump to a delivery site in the patient.

SUMMARY

In general, the disclosure describes techniques for managing fluid delivery with multiple fluid reservoirs. The fluid delivery device includes at least two different therapeutic fluid reservoirs connected to a single inlet port. A fluid delivery needle can be inserted into the inlet port to selectively access both of the at least two different therapeutic fluid reservoirs. In some examples, the inlet port includes a sensor configured to detect entry of the fluid delivery needle. The sensor may confirm that the user has accessed the inlet port. The sensor may also confirm that the user has accessed the correct fluid reservoir via the inlet port. In additional examples, the fluid delivery device may include various valve configurations for withdrawing therapeutic fluid from at least two different reservoirs for delivery through a fluid delivery pump.

In one example, this disclosure describes a therapeutic fluid delivery system that includes a first reservoir configured to house a first therapeutic fluid, a second reservoir configured to house a second therapeutic fluid, and an inlet port configured to receive a fluid delivery needle. The first therapeutic fluid and second therapeutic fluid may be the same therapeutic fluid or different therapeutic fluids. The inlet port is configured for fluid communication between the fluid delivery needle and the first reservoir, and the inlet port is further configured for fluid communication between the fluid delivery needle and the second reservoir. In some examples, the inlet port includes a first septum and a second septum. Further, the inlet port is configured for fluid communication between the fluid delivery needle and the first reservoir when the fluid delivery needle penetrates the first septum and fluid communication between the fluid delivery needle and the second reservoir when the fluid delivery needle penetrates the second septum.

In another example, a method includes inserting a fluid delivery needle into an inlet port of a fluid delivery device. The inlet port is configured for fluid communication between the fluid delivery needle and a first reservoir configured to house a first therapeutic fluid, and the inlet port is further configured for fluid communication between the fluid delivery needle and a second reservoir configured to house a second therapeutic fluid.

In another example, a computer-readable storage medium contains instructions that cause a programmable processor to cause a sensor to detect a characteristic that varies as a fluid delivery needle penetrates at least one of a first septum and second septum in an inlet port of a fluid delivery device. The instructions also cause the programmable processor to determine when the fluid delivery needle penetrates the at least one of the first septum and second septum based on the detected characteristic. In the example, the inlet port is configured for fluid communication between the fluid delivery needle and a first reservoir configured to house a first therapeutic fluid, and the inlet port is further configured for fluid communication between the fluid delivery needle and a second reservoir configured to house a second therapeutic fluid.

In another example, a fluid delivery system includes means for delivering fluid to a fluid delivery device. The fluid delivery device includes a first reservoir configured to house a first therapeutic fluid and a second reservoir configured to house a second therapeutic fluid. The fluid delivery system also includes means for receiving the means for delivering fluid, where the first reservoir and the second reservoir are in fluid communication with the means for receiving.

The details of one or more examples of the invention are set forth in the accompanying drawings and the description below. Other features, objects, and advantages will be apparent from the description and drawings, and from the claims.

DETAILED DESCRIPTION

Figure 1:
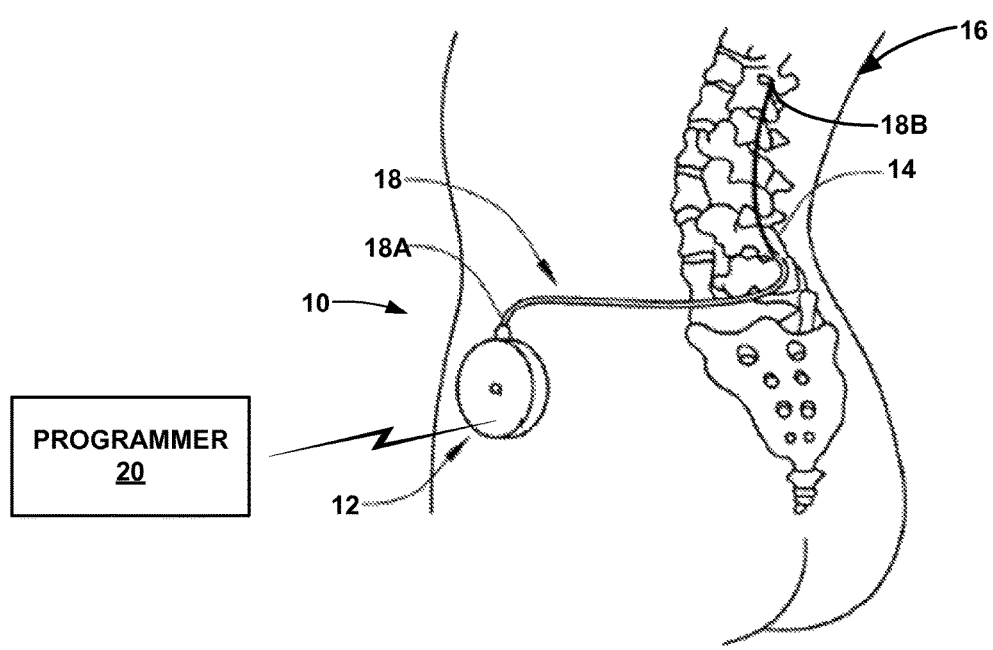
FIG. 1 is a conceptual diagram illustrating an example of a fluid delivery system including an implantable fluid delivery device configured to deliver a therapeutic fluid to a patient via a catheter.

An implantable fluid delivery device may be implanted in the body of a patient to deliver a fluid, such as a drug or other therapeutic agent, through a catheter to one or more selected delivery sites within the body of the patient. The implantable fluid delivery device may include one or more reservoirs for storing the therapeutic agents prior to delivery to a patient. In some examples, the implantable fluid delivery device includes at least two reservoirs to allow the user to store different therapeutic agents, different concentrations of the same therapeutic agent, or different quantities of agents. The implantable fluid delivery device may also include an inlet port, such as a refill port, to facilitate in-service refilling of the fluid reservoir over the service life of the implantable fluid delivery device, e.g., via a percutaneous, hypodermic syringe needle. To refill multiple reservoirs, the implantable fluid delivery device may include a separate inlet port for each reservoir, thus providing a dedicated access site for each reservoir to add or withdraw therapeutic agent.

It would generally be useful for the safe and intended operation of the fluid delivery device if a user, such as a patient or clinician, could readily distinguish between different inlet ports that are connected to different reservoirs. Different inlet ports may be located on different sides of the fluid delivery device to distinguish one inlet port from another inlet port. In some examples, a user may rely on the physical geometry of the fluid delivery device and tactile feel to distinguish between different inlet ports on the fluid delivery device. In other examples, a user may employ an external aid, such as a template, to identify and distinguish between different inlet ports on the fluid delivery device.

In accordance with the techniques described in this disclosure, a fluid delivery device with at least one inlet port connected to at least two different therapeutic fluid reservoirs is provided. A fluid delivery needle, such as a hypodermic needle, can be inserted into the at least one inlet port to selectively access both of the at least two different therapeutic fluid reservoirs. In this manner, multiple fluid reservoirs are accessible through a single inlet port, reducing the number of inlet ports required on a multi-reservoir fluid delivery device. A fluid delivery device with fewer inlet ports may be more user friendly than a comparable fluid delivery device with more inlet ports.

In some examples according to this disclosure, an inlet port includes a sensor configured to detect entry of the fluid delivery needle. The sensor may confirm that the user has accessed the inlet port. The sensor may also confirm that the user has accessed the correct fluid reservoir, for example, where an inlet port connects to at least two fluid reservoirs. Alternatively, the sensor may be configured to detect when the fluid delivery needle is withdrawn from the inlet port including, e.g., when the needle is accidentally withdrawn. As a result, the sensor can help monitor the integrity of a therapeutic fluid refilling operation.

Because a user generally intends that a therapeutic fluid added to different reservoirs of a multi-reservoir fluid delivery pump will be delivered through the pump, this disclosure also provides examples of valve configurations for withdrawing therapeutic fluid from at least two different reservoirs. In some examples, a single controllable valve is used to provide selectable fluid access to at least two different reservoirs. In other examples, multiple valves are used to control fluid delivery from multiple reservoirs. For example, a fluid delivery device may include an active, controllable valve and a passive valve to separately control fluid delivery from two different reservoirs.

Figure 5A:
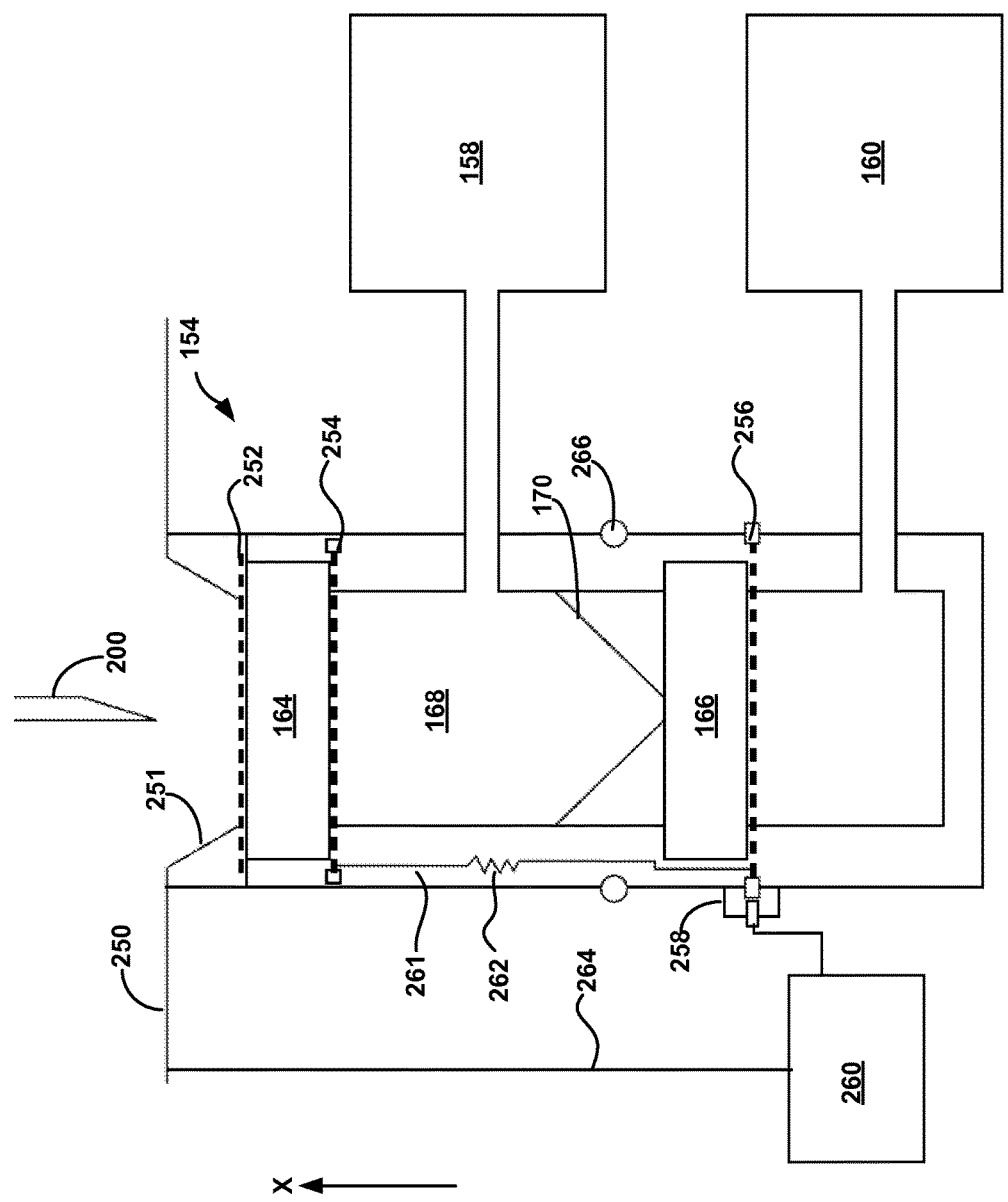
FIG. 5A is a conceptual diagram illustrating an example inlet port for the example implantable fluid delivery device of FIG. 4.
Figure 5B:
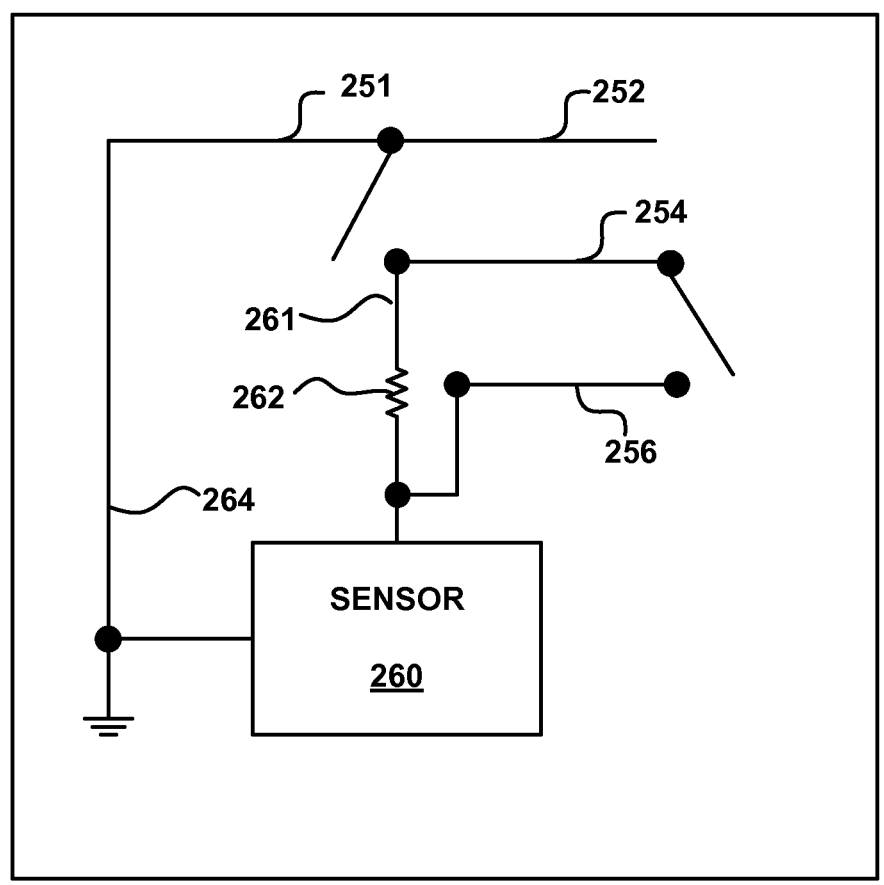
FIG. 5B is an equivalent circuit diagram for the example inlet port of FIG. 5A.
Figure 6:
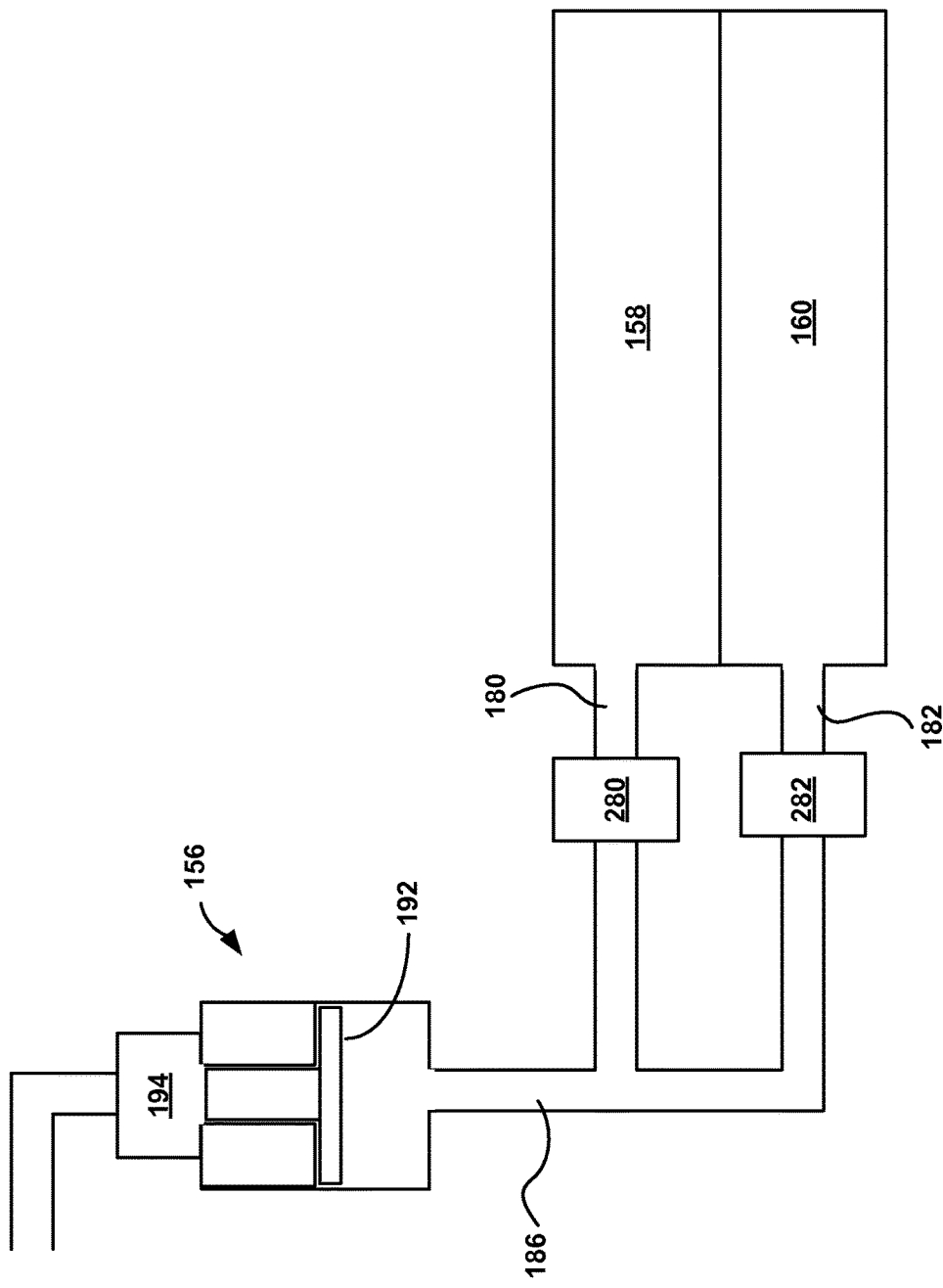
FIG. 6 is a functional block diagram of an example reservoir outlet valve configuration for the example implantable fluid delivery device of FIG. 4.

Example fluid therapy delivery device inlet port, reservoir, and valve configurations will be described in greater detail with reference to FIGS. 4-6. However, an example fluid delivery system including an implantable fluid delivery device and external programmer will first be described with reference to FIGS. 1-3.

FIG. 1 is a conceptual diagram illustrating an example of a therapy system 10, which includes implantable medical device (IMD) 12, catheter 18, and external programmer 20. IMD 12 is connected to at least one catheter 18 to deliver at least one therapeutic fluid, e.g. a pharmaceutical agent, pain relieving agent, anti-inflammatory agent, gene therapy agent, or the like, to a target site within patient 16. IMD 12 includes an outer housing that, in some examples, is constructed of a biocompatible material that resists corrosion and degradation from bodily fluids including, e.g., titanium or biologically inert polymers. IMD 12 may be implanted within a subcutaneous pocket relatively close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic fluid. In still other examples, device 12 may be external to patient 16 with a percutaneous catheter connected between IMD 12 and the target delivery site within patient 16. In these examples, device 12 is not an implantable medical device but rather an external medical device.

As described in greater detail below, IMD 12 includes at least two reservoirs for housing therapeutic fluid. In one example, IMD 12 includes at least one inlet port for adding or withdrawing fluid from each of the at least two reservoirs. For example, in some cases, IMD 12 includes at least two septa in a stacked arrangement. Penetrating different septa by, e.g., inserting a fluid delivery needle through different septa in the stacked arrangement, provides fluid access to different reservoirs. A first septum may be positioned at a first depth accessible via the access port, and a second septum may be positioned at a second depth accessible via the same access port. In another example, IMD 12 includes one or more valves interposed between a fluid reservoir and a fluid delivery pump. Selective actuation of the one or more valves allows IMD 12 to draw fluid from different reservoirs for delivery to patient 16.

IMD 12 delivers a therapeutic fluid from a reservoir (not shown) to patient 16 through catheter 18 from proximal end 18A coupled to IMD 12 to distal end 18B located proximate to the target site. Example therapeutic fluids that may be delivered by IMD 12 include, e.g., insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy drugs or agents, anticoagulants, cardiovascular medications or chemotherapeutics.

Catheter 18 can comprise a unitary catheter or a plurality of catheter segments connected together to form an overall catheter length. In addition, catheter 18 may be a single-lumen catheter or a multi-lumen catheter. Catheter 18 may be coupled to IMD 12 either directly or with the aid of a catheter extension (not shown in FIG. 1). In the example shown in FIG. 1, catheter 18 traverses from the implant site of IMD 12 to one or more targets proximate to spinal cord 14, e.g., within an intrathecal space or epidural space. Catheter 18 is positioned such that one or more fluid delivery outlets (not shown in FIG. 1) of catheter 18 are proximate to the targets within patient 16. In the example of FIG. 1, IMD 12 delivers a therapeutic fluid through catheter 18 to one or more targets proximate to spinal cord 14.

IMD 12 can be configured for intrathecal drug delivery into the intrathecal space, as well as epidural delivery into the epidural space, both of which surround spinal cord 14. In some examples, multiple catheters may be coupled to IMD 12 to target the same or different nerve sites or other tissue sites within patient 16, or catheter 18 may include multiple lumens to deliver multiple therapeutic fluids to the patient. Therefore, although the target site shown in FIG. 1 is proximate to spinal cord 14 of patient 16, other applications of therapy system 10 may include alternative target delivery sites in addition to or in lieu of the spinal cord of the patient. For example, therapy system 10 may be configured to deliver single or multisite deep-brain infusion therapy.

Programmer 20 is an external computing device that is configured to communicate with IMD 12 by wireless telemetry as needed, such as to provide or retrieve therapy information or control aspects of therapy delivery (e.g., modify the therapy parameters such as rate or timing of delivery, turn IMD 12 on or off, and so forth) from IMD 12 to patient 16. In some examples, programmer 20 may be a clinician programmer that the clinician uses to communicate with IMD 12 and to program therapy delivered by IMD 12. Alternatively, programmer 20 may be a patient programmer that allows patient 16 to view and modify therapy parameters associated with therapy programs. The clinician programmer may include additional or alternative programming features than the patient programmer. For example, more complex or sensitive tasks may only be allowed by the clinician programmer to prevent patient 16 from making undesired or unsafe changes to the operation of IMD 12. Programmer 20 may be a handheld or other dedicated computing device, or a larger workstation or a separate application within another multi-function device.

As described in greater detail below with reference to FIGS. 4 and 5, IMD 12, alone or in cooperation with programmer 20 or another external device communicatively connected to IMD 12, is configured to detect entry of a fluid delivery needle into an inlet port. In one example, programmer 20 provides an indication when a fluid delivery needle penetrates a septum. In another example, programmer 20 provides an indication when a fluid delivery needle is withdrawn from a septum. An indication provided via programmer 20 includes, in different examples, an audible, tactile, and/or visual indication.

Figure 2:
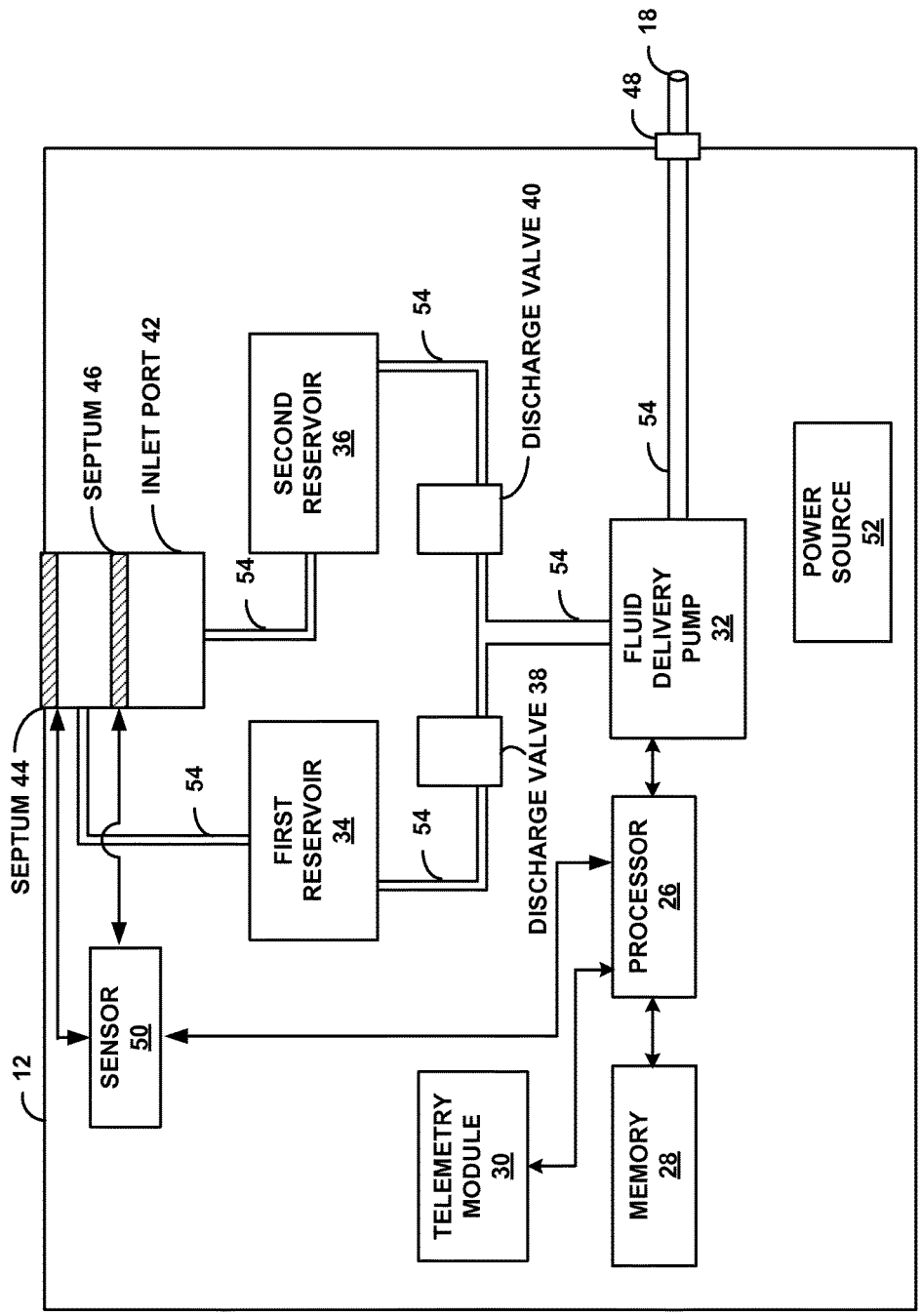
FIG. 2 is a functional block diagram illustrating an example of the implantable fluid delivery device of FIG. 1.

FIG. 2 is a functional block diagram illustrating components of an example of IMD 12, which includes processor 26, memory 28, telemetry module 30, fluid delivery pump 32, first reservoir 34, second reservoir 36, first reservoir discharge valve 38, second reservoir discharge valve 40, inlet port 42, first septum 44, second septum 46, catheter access port 48, power source 52, and internal fluid pathways 54. Processor 26 is communicatively connected to memory 28, telemetry module 30, fluid delivery pump 32, and sensor 50. Processor 26 may also be communicatively coupled to first reservoir discharge valve 38 and/or second reservoir discharge valve 40. Fluid delivery pump 32 may be connected to first reservoir 34 and second reservoir 36 through fluid pathways 54 and reservoir discharge valves 38, 40, respectively. Reservoirs 34, 36 are connected to inlet port 42 though fluid pathways 54. Inlet port 42 includes first septum 44 and second septum 46. Catheter access port 48 is connected to catheter 18.

IMD 12 also includes power source 52, which is configured to deliver operating power to various components of the IMD. In some examples, IMD 12 may include more than two reservoirs 34, 36 (e.g., three, four, five or more reservoirs) for storing more than two types of therapeutic fluid or for storing different amounts of therapeutic fluid. Further, as described in greater detail with respect to FIG. 4, IMD 12 may include a single reservoir discharge valve in addition to, or in lieu of, two reservoir discharge valves 38, 40. However, for ease of description, IMD 12 in FIG. 2 includes two reservoirs 34, 36 in fluid communication with two separate reservoir discharge valves 38, 40.

During operation of IMD 12, processor 26 controls fluid delivery pump 32 with the aid of instructions associated with program information that is stored in memory 28 to deliver a therapeutic fluid to patient 16 via catheter 18. Instructions executed by processor 26 may, for example, define therapy programs that specify the dose of therapeutic fluid that is delivered to a target tissue site within patient 16 from first reservoir 34 and/or second reservoir 36 via catheter 18. The programs may further specify a schedule of different therapeutic fluid rates and/or other parameters by which IMD 12 delivers therapy to patient 16. In some examples, the programs specify valve actuation commands for controlling first reservoir discharge valve 38 and/or second reservoir discharge valve 40. In some examples, various instructions, such as instructions that define therapy programs, may be stored in a memory of an external device communicatively connected to IMD 12. In one example, therapy program instructions are stored in a memory of programmer 20 and communicated to processor 26 via telemetry module 30.

In general, a therapy program stored on memory 28 and executed by processor 26 defines one or more therapeutic fluid doses to be delivered from first reservoir 34 and/or second reservoir 36 to patient 16 through catheter 18 by IMD 12. A dose of therapeutic fluid generally refers to a total amount of therapeutic fluid, e.g., in volumetric units, delivered over a total amount of time, e.g., twenty-four hour period. The amount of therapeutic fluid in a dose may convey to a caregiver an indication of the probable efficacy of the fluid and the possibility of side effects.

In general, a sufficient amount of the fluid should be administered in order to have a desired therapeutic effect, such as pain relief. However, the amount of the therapeutic fluid delivered to the patient may be limited to a maximum amount, such as a maximum daily amount, in order not to avoid potential side effects. Therapy program parameters specified by a user, e.g., via programmer 20 may include the type of therapeutic fluid (e.g., when different types of fluid are housed in reservoir 34 and 36), fluid volume per dose, dose time period, maximum dose for a given time interval e.g., daily. In some examples, dosage may also prescribe particular concentrations of active ingredients in the therapeutic fluid delivered by IMD 12 to patient 16.

The manner in which a dose of therapeutic fluid is delivered to patient 16 by IMD 12 may also be defined in the therapy program. For example, processor 26 of IMD 12 may be programmed to deliver a dose of therapeutic fluid according to a schedule that defines different rates at which the fluid is to be delivered at different times during the dose period, e.g. a twenty-four hour period. The therapeutic fluid rate refers to the amount, e.g. in volume, of therapeutic fluid delivered over a unit period of time, which may change over the course of the day as IMD 12 delivers the dose of fluid to patient 16. As an example, processor 26 of IMD 12 may be programmed to deliver a dose of different therapeutic fluids, e.g., according to a schedule that defines times and rates for delivering different therapeutic fluids. In one example, processor 26 of IMD 12 is configured to mix different therapeutic fluids, e.g., based on mixing ratios specified in a look-up table stored in memory 28, to deliver a composite therapeutic fluid based on therapeutic fluids housed in both reservoir 34 and reservoir 36. In another example, processor 26 of IMD 12 is configured to deliver time interleaved doses of different fluids from first reservoir 34 and second reservoir 36. In various examples, processor 26 of IMD 12 may be programmed to deliver therapeutic fluid solely from first reservoir 34, solely from second reservoir 36, or to switch between delivering therapeutic fluid from first reservoir 34 and second reservoir 36.

As one example, IMD 12 could be programmed to deliver therapeutic fluid from first reservoir 34 to patient 16 at a rate of 20 microliters per hour. In the event the therapy program prescribes this fluid delivery rate for a twenty four hour period and assuming no patient or other boluses during the period of time, the dose of fluid delivered to patient 16 by IMD 12 will be 480 microliters (per twenty four hours). As another example, IMD 12 could be programmed to deliver therapeutic fluid from first reservoir 34 to patient 16 at a rate of eight microliters per hour for a period of six hours followed by therapeutic fluid from second reservoir 36 at a rate of sixteen microliters per hour for a period of eighteen hours. Assuming no additional therapeutic fluid is delivered to patient 16, the dose of fluid delivered to patient 16 by IMD 12 will be 336 microliters (per twenty four hours). In each example, the therapy program may include other parameters, including, e.g., definitions of priming and patient boluses, as well as time intervals between successive patient boluses, sometimes referred to as lock-out intervals.

Therapy programs may be a part of a program group, where the group includes a number of therapy programs. Memory 28 of IMD 12 or a memory associated with programmer 20 may store one or more therapy programs, as well as instructions defining the extent to which patient 16 may adjust therapy parameters, switch between therapy programs, or undertake other therapy adjustments. Patient 16 or a clinician may select and/or generate additional therapy programs for use by IMD 12, e.g., via programmer 20 at any time during therapy or as designated by the clinician.

Components described as processors within IMD 12, external programmer 20, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination.

In one example, processor 26 of IMD 12 is programmed to deliver a dose of therapeutic fluid to patient 16, which is defined in memory 28 of the device by a volume of therapeutic fluid delivered to the patient in one day. IMD 12 is also programmed according to a therapy schedule such that the different fluids are delivered at different rates at different times during the day, which may be stored in the device memory, e.g., as a look-up table associating different fluids, different fluid rates and different times of the day.

Upon instruction from processor 26, first reservoir discharge valve 38 and/or second reservoir discharge valve 40 actuates open, fluid delivery pump 32 draws fluid from first reservoir 34 and/or second reservoir 36 and pumps the fluid through fluid pathway 54 to catheter 18, e.g., in accordance with a program stored on memory 28.

Fluid pathways 54 in IMD 12 may be segments of tubing or ducts within IMD 12 that allow fluid to be conveyed through IMD 12. In some examples, fluid pathways 48 may be machined or cast into IMD 12. Fluid pathways 54 are created from a biocompatible material, e.g., titanium, stainless steel, or biologically inert polymer, and sized, e.g., to accommodate desired flow rates in IMD 12.

First reservoir discharge valve 38 and second reservoir discharge valve 40 are configured to control fluid communication between reservoirs 34, 36 and fluid delivery pump 32, respectively. In some examples, at least one of valves 38, 40 is communicatively coupled to processor 26 for actuation control. In some examples, both valve 38 and valve 40 are communicatively coupled to processor 26 for actuation control. During operation, the communicatively coupled valve receives instructions from processor 26 to, e.g., actuate in order to open or close a fluid pathway 54 connecting reservoirs 34, 36 to fluid delivery pump 32. In general, valves 38, 40 may be any device that regulates the flow of a fluid by opening, closing, or partially obstructing fluid pathway 54. Example valves are described in greater detail with respect to FIGS. 4 and 6.

First reservoir 34 and second reservoir 36 are generally sized to house enough fluid to allow patient 16 to receive therapeutic dosing without continuously refilling the reservoirs. In some examples, first reservoir 34 and second reservoir 36 are each sized based, e.g., on the shelf-life of the fluid expected to be housed in reservoir 34, 36, or the anticipated delivery rate of the fluid expected to be housed in reservoir 34, 36. In one example, first reservoir 34 and second reservoir 36 may each house between approximately 5 milliliters and approximately 120 milliliters, such as between approximately 15 milliliters and approximately 75 milliliters. In some examples, first reservoir 34 and second reservoir 36 are the same size, while in other examples, first reservoir 34 and second reservoir 34 are different sizes.

First reservoir 34 and second reservoir 36 may house the same therapeutic fluid, e.g., in different quantities of or different concentrations, to provide therapy dosing flexibility. Alternatively, first reservoir 34 and second reservoir 36 may house different therapeutic fluids, e.g., to achieve different therapeutic effects or to provide different fluid storage conditions, such as acidic and basic pH storage conditions. In general, first reservoir 34 and second 36 may be arranged in numerous locations within IMD 12 including, e.g., a stacked arrangement (e.g., one on top of another) or a coplanar arrangement (e.g., side-by-side) to minimize the overall thickness of IMD 12.

IMD 12 includes fluid delivery pump 32. Fluid delivery pump 32 can be any mechanism that delivers a therapeutic fluid in some metered or other desired flow dosage to the therapy site within patient 16 from reservoir 34 and/or 36 via implanted catheter 18. Fluid delivery pump 32 can be an active pump that allows volumetric flow rates to be manipulated and controlled, e.g., as part of a therapy delivery program or upon receiving instructions from programmer 20. Fluid delivery pump 32 can also be a passive pump that provides a constant volumetric flow rate, with overall fluid delivery controlled by cycling fluid delivery pump 32 on and off. In some examples, IMD 12 may include a plurality of pumps (e.g., two, three, four pumps) that operate at similar parameters, e.g., pressure and volumetric flow rate, or different parameters. According to one example, first reservoir 34 and second reservoir 36 are connected to different pumps that separately draw fluid from either first reservoir 34 or second reservoir 36 for delivery through catheter 18 to patient 16. In another example, first reservoir 34 and second reservoir 36 are connected to different pumps that separately draw fluid from first reservoir 34 and second reservoir 36 for delivery through separate fluid lumens, e.g., different catheters or different lumens of a multi-lumen catheter 18. In this manner, IMD 12 can be configured to provide isolated fluid pathways from first reservoir 34 and second reservoir 36 to patient 16, which may be desirable for various reasons including, e.g., to prevent mixing of incompatible fluids or to allow simultaneous fluid delivery to two separate regions of patient 16.

In various examples, fluid delivery pump 32 may be an axial pump, a centrifugal pump, a pusher plate pump, a piston-driven pump, or other means for moving fluid through internal fluid pathway 54 and catheter 18. In one example, fluid delivery pump 32 is an electromechanical pump that delivers fluid by the application of pressure generated by a piston that moves in the presence of a varying magnetic field and that is configured to draw fluid from reservoir 34 and/or 36 and pump the fluid through fluid pathway 54 and catheter 18 to patient 16. In another example, fluid delivery pump 32 is a squeeze pump that squeezes fluid pathway 54 in a controlled manner, e.g., such as a peristaltic pump, to progressively move fluid from reservoir 34 and/or 36 to the distal end of catheter 18 and then into patient 16 according to parameters specified by the therapy program stored on memory 28 and executed by processor 26.

Periodically, fluid may need to be percutaneously added or withdrawn from IMD 12. Fluid may need to be withdrawn from reservoir 34 and/or 36 if a clinician wishes to replace an existing fluid with a different fluid or a similar fluid with different concentrations of therapeutic agents. Fluid may also need to be added to reservoir 34 and/or 36 if all therapeutic fluid has been or will be deliver to patient 16. Inlet port 42 provides access for adding or withdrawing fluid from IMD 12 through septum 44 and septum 46. Inlet port 42 is located on a peripheral surface of a housing of IMD 12, e.g., centered on a housing surface accessible to percutaneous entry, and is in fluid communication with first reservoir 34 and second reservoir 36. Inlet port 42 may define an access aperture for percutaneously accessing septum 44 alone, or septum 44 and septum 46, on a selective basis. Septa 44 and 46 may be self-sealing members, e.g., formed from a deformable biocompatible polymer, that prevent loss of therapeutic fluid delivered to reservoir 34 or 36 via inlet port 42. Septa 44 and 46 are accessible using a percutaneous delivery system, e.g., a hypodermic syringe with a fluid delivery needle configured to penetrate septa 44 and 46. The fluid delivery needle is placed in fluid communication with first reservoir 34 by inserting the needle through first septum 44, but not second septum 46. Alternatively, the fluid delivery needle is placed in fluid communication with the second reservoir 36 by inserting the needle through both first septum 44 and second septum 46. Hence, the depth of insertion of the needle determines which reservoir is accessed. Septa 44 and 46 may seal shut when the needle is removed from inlet port 42.

In the example of FIG. 2, IMD 12 includes sensor 50 communicatively coupled to processor 26. Sensor 50 may be configured to detect a characteristic that varies when a fluid delivery needle penetrates either first septum 44 and/or second septum 46. In some examples, IMD 12 may include multiple sensors, e.g., to measure different characteristics or to detect needle entry at different septa. Sensor 50 may be arranged in various locations within IMD 12 including, e.g., in direct communication with septa 44 and 46 (as shown in FIG. 2) or fluid pathways 54 between inlet port 42 and reservoirs 34 and 36. Sensor 50 may be any device capable of detecting a characteristic that varies with fluid delivery needle penetration, some of which are described in greater detail below with respect to FIGS. 4 and 5. In one example, septa 44 and 46 include an electrically conductive material, and sensor 50 is configured to detect an electrical characteristic that changes when a fluid delivery needle penetrates a septum. In another example, sensor 50 is configured to detect a pressure pulse caused by needle penetration of septum 44 and/or 46. In various examples, sensor 50 may be a voltmeter, ampmeter, ohmmeter, pressure sensor, flow sensor, capacitive sensor, acoustic sensor, optical sensor, or the like. Sensor 50 generates a signal that varies when a fluid delivery needle penetrates a septum, and the signal is transmitted to processor 26 for, e.g., analysis and storage on memory 28. In general, the same characteristic that varies when a fluid delivery needle penetrates either first septum 44 and/or second septum 46 may also vary when the fluid delivery needle is withdrawn from either first septum 44 and/or second septum 46.

Processor 26 of IMD 12, alone or in conjunction with a processor of programmer 20 or another device communicatively connected to IMD 12, may be configured to analyze a signal generated by sensor 50 to determine when a fluid delivery needle penetrates either first septum 44 or second septum 46. In some examples, processor 26 compares new values for the detected characteristic (e.g., after penetration) to previously established values for the detected characteristic (e.g., before penetration) stored on memory 28 to determine if a fluid delivery needle penetrated or is withdrawn from either first septum 44 or second septum 46. In other examples, processor 26 compares values for the detected characteristic to an absolute value, e.g., stored in a look-up table in memory 28, to determine if a fluid delivery needle penetrated or is withdrawn from either first septum 44 or second septum 46. In any event, processor 26 may transmit a message via telemetry module 30, e.g., to programmer 20, when a needle penetrates, e.g., first septum 44. Processor 26 may transmit a separate message when the needle penetrates second septum 46. In a different example, processor 26 transmits a message when a needle is withdrawn from septum 46 and again when the needle is withdrawn from septum 44. In response to receiving a message from IMD 12, programmer 20, or another device communicatively coupled to IMD 12, may provide a user indication, e.g., indicating that a fluid delivery needle penetrated a certain septum or that a fluid delivery needle was withdrawn from a certain septum. In this manner, IMD 12 provides septum awareness to assist a user attempting to refill a reservoir in IMD 12.

In general, awareness of different properties within IMD 12 including, e.g., fluid flow rates, pressures, temperatures, volumes, and the like, may be desirable to monitor the operation of IMD 12. Consequently, IMD 12, in various examples, may include a different sensor (not shown) in addition to, or in lieu of, sensor 50. The sensor may be arranged in a number of locations within IMD 12, including, e.g., in first reservoir 34, second reservoir 36, or fluid pathway 54. In some examples, the sensor is configured to measure a fluid characteristic in IMD 12. In some examples, the sensor may include a pressure sensor, flow sensor, pH sensor, temperature sensor or the like. In any event, IMD 12 may include multiple sensors, e.g., to measure different fluid characteristics or to measure fluid characteristics in multiple locations.

In general, memory 28 stores program instructions and related data that, when executed by processor 26, cause IMD 12 and processor 26 to perform the functions attributed to them in this disclosure. For example, memory 28 of IMD 12 may store instructions for execution by processor 26 including, e.g., therapy programs, programs for actuating valve 38 and/or 40, programs for monitoring and comparing a signal generated by sensor 50, and any other information regarding therapy delivered to patient 16 and/or the operation of IMD 12. Memory 28 may include separate memories for storing instructions, patient information, therapy parameters, therapy adjustment information, program histories, and other categories of information such as any other data that may benefit from separate physical memory modules. Therapy adjustment information may include information relating to timing, frequency, rates and amounts of patient boluses or other permitted patient modifications to therapy.

In some examples, processor 26 of IMD 12 may collect and store measurements made by sensor 50 or another sensor of IMD 12 in memory 28 and/or in a memory associated with an external device communicatively coupled to IMD 12, such as programmer 20. In various examples, a memory may store data that includes, e.g., a time and date stamp when septum 44 is penetrated, a time and date stamp when septum 46 is penetrated, a time and date stamp when a needle is withdrawn from septum 46, a time and date stamp when a needle is withdrawn from septum 44, data corresponding to fluid filling or withdrawal rates, and the like. By storing the various sensor data, IMD 12 may allow a clinician to evaluate the utilization of IMD 12 and to determine whether IMD 12 is being appropriately accessed through inlet port 42.

At various times during the operation of IMD 12 to treat patient 16, communication to and from IMD 12 may be necessary to, e.g., change therapy programs, adjust parameters within one or more programs, configure or adjust a particular bolus, or to otherwise download information to or from IMD 12. Processor 26 controls telemetry module 30 to wirelessly communicate between IMD 12 and other devices including, e.g. programmer 20. Telemetry module 30 in IMD 12, as well as telemetry modules in other devices described in this disclosure, such as programmer 20, can be configured to use RF communication techniques to wirelessly send and receive information to and from other devices respectively according to standard or proprietary telemetry protocols. In addition, telemetry module 30 may communicate with programmer 20 via proximal inductive interaction between IMD 12 and the external programmer. Telemetry module 30 may send information to external programmer 20 on a continuous basis, at periodic intervals, or upon request from the programmer.

Power source 52 delivers operating power to various components of IMD 12. Power source 52 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As another alternative, an external inductive power supply can transcutaneously power IMD 12 as needed or desired.

Figure 3:
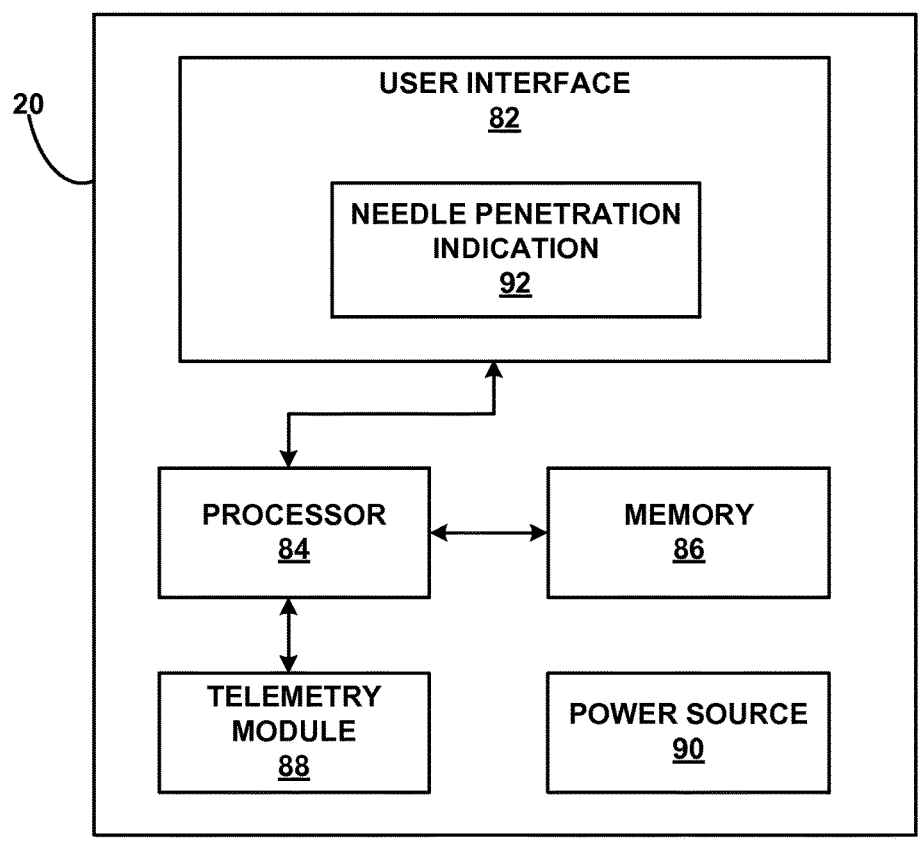
FIG. 3 is a functional block diagram illustrating an example of an external programmer shown in FIG. 1.

As described, IMD 12 may communicate with one or more external devices at various times during the operation of IMD 12. In the example of FIG. 1, IMD 12 communicates with external programmer 20. FIG. 3 is a functional block diagram illustrating an example of various components of external programmer 20. As shown in FIG. 3, external programmer 20 may include user interface 82, processor 84, memory 86, telemetry module 88, and power source 90. A clinician or patient 16 interacts with user interface 82 to change the parameters of a therapy program, change therapy programs within a group of programs, view therapy information, view historical or establish new therapy programs, or otherwise communicate with IMD 12 or view or edit programming information. Processor 84 controls user interface 82, retrieves data from memory 86 and stores data within memory 86. Processor 84 also controls the transmission of data through telemetry module 88 to IMD 12. The transmitted data may include, e.g., instructions assigning particular therapeutic fluids to first reservoir 34 and second reservoir 36. The transmitted data may also include therapy program information specifying various therapeutic fluid delivery parameters. For example, transmitted data may specify a reservoir or sequence of reservoirs, e.g., by specifying reservoir discharge valve actuation commands, to enable fluid delivery pump 32 to selectively deliver fluids from first reservoir 34 and second reservoir 36. Memory 86 may store, e.g., operational instructions for processor 84 and data related to therapy for patient 16.

Programmer 20 may be a hand-held computing device that includes user interface 82 that can be used to provide input to programmer 20. User interface 82 may generally include a display screen or other output media, and user input media. In a variety of examples, programmer 20 may provide visual, audible, and/or tactile indications.

User interface 82 may be configured to present therapy program information to the user as graphical bar graphs or charts, numerical spread sheets, or in any other manner in which information may be displayed. In addition, user interface 82 may be configured to present IMD 12 hardware configuration information including, e.g., septum information, discharge valve information, fluid pathway information, reservoir information, pump information, refill information, or the like to the user in text or graphical display form. The information may generally indicate, e.g., that a septum is being penetrated by a fluid delivery needle, a needle is being withdrawn from a septum, a discharge valve is actuated to specific position, a fluid pathway is open or closed, a reservoir is filling or discharging, reservoir fill levels (e.g., volume levels), or that a pump is operating. In some examples, the information may include operating statistics including, e.g., flow rates, pressures, temperatures, volumes, or the like.

In one example, user interface 82 may display a visual, e.g., graphical or textual, representation of inlet port 42 including septa 44 and 46, reservoir fluid pathways 54, and reservoirs 34 and 36. User interface 82 may also display a visual graphic of a fluid delivery needle when septum 44 or 46 is penetrated. Portions of the visual graphic may change color, shape, size, or the like to, e.g., indicate that a septum is being penetrated by a fluid delivery needle, a needle is being withdrawn from a septum, or the fluid is flowing into or out of first reservoir 34 or second reservoir 36. In some further examples, user interface 82 may present nominal or suggested therapy parameters that the user may accept via user interface 82. User interface 82 also provides input mechanisms to enable the user to program IMD 12 in accordance with one or more therapy programs or otherwise provide data to IMD 12 necessary for delivering therapy to patient 16.

When programmer 20 is configured for use by a clinician, user interface 82 may be used to transmit initial programming information to IMD 12 including hardware information for system 10, e.g. the number of reservoirs 34, 36, the number of fluid delivery pumps 32, the number and type of discharge valves 38, 40, the position of fluid pathways 54, a baseline orientation of at least a portion of IMD 12 relative to a reference point, and software information related to therapy delivery and operation of IMD 12, e.g., parameters for controlling valve 38 and/or 40, therapy parameters of therapy programs stored within IMD 12 or within programmer 20, the type and amount, e.g., by volume of therapeutic fluid(s) delivered by IMD 12 and any other information the clinician desires to program into IMD 12.

Programmer 20 may also be configured for use by patient 16. When configured as a patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

In the example of FIG. 3, user interface 82 of programmer 20, whether employed as a patient or clinician programmer, includes needle penetration indication 92. Whether controlled by processor 26 of IMD 12, as described above, or processor 84 of programmer 20, needle penetration indication 92 is configured to indicate whether a fluid delivery needle is penetrating septum 44 and/or 46, whether a needle has penetrated septum 44 and/or 46 without being withdrawn, or whether a needle is being withdrawn from septum 44 and/or 46. In this regard, a needle penetration indication may also be considered a needle withdrawal indication. Needle penetration indication 92 may include any combination of text or graphical representations of inlet port 42 and septa 44 and 46. For example, needle penetration indication 92 may include icons representative of inlet port 42, septa 44 and 46, and a fluid delivery needle. The icons may be colored, filled in, highlighted, increase and decrease in size, or otherwise vary based, e.g., on the position of the fluid delivery needle, whether the needle is penetrating or being withdrawn from a septum, or whether a specific septum is penetrated. Needle penetration indication 92 may also include an audible or tactile indication in conjunction with, or in lieu of, a visual indication. In one example, programmer 20 issues an audible command when septum 44 is penetrated and again when septum 46 is penetrated. In various examples, an audible command may include negative signals, e.g., "warning," "wrong reservoir accessed," "terminate refill operation," "needle unexpectedly withdrawn," or the like, or positive command prompts, e.g., "ready to refill first reservoir," "ready to refill second reservoir," "morphine reservoir accessed," or the like. In another example, programmer 20 vibrates when septum 44 is penetrated and again when septum 46 is penetrated. In some examples, programmer 20 issues a different indication when a needle is withdrawn from a septum than when a needle penetrates a septum. For example, programmer 20 may vibrate when septum 44 is penetrated but issue an audible chirp when a needle is withdrawn from septum 44.

As described, processor 26 of IMD 12 may collect and store measurements made by sensor 50 or another sensor of IMD 12 in memory 28. An external instrument, e.g. a patient programmer, may automatically pull data captured by sensor 50 or another sensor of IMD 12 from memory 28 via telemetry modules 30 and 88 on a regular basis. In another example, a clinician programmer may pull measurements made by sensor 50 or another sensor of IMD 12 from memory 28 via telemetry modules 30 and 88 on a patient visit. In either case, processor 84 may store the data captured by sensor 50 or another sensor of IMD 12 in memory 86 and may employ the data to analyze the utilization of IMD.

Telemetry module 88 allows the transfer of data to and from programmer 20 and IMD 12, as well as other devices, e.g. according to the RF communication techniques described above with reference to FIG. 2. Power source 90 may be a non-rechargeable battery or a rechargeable battery, such as a lithium ion or nickel metal hydride battery. In some examples, programmer 20 may be configured to recharge IMD 12 in addition to programming IMD 12.

Figure 4:
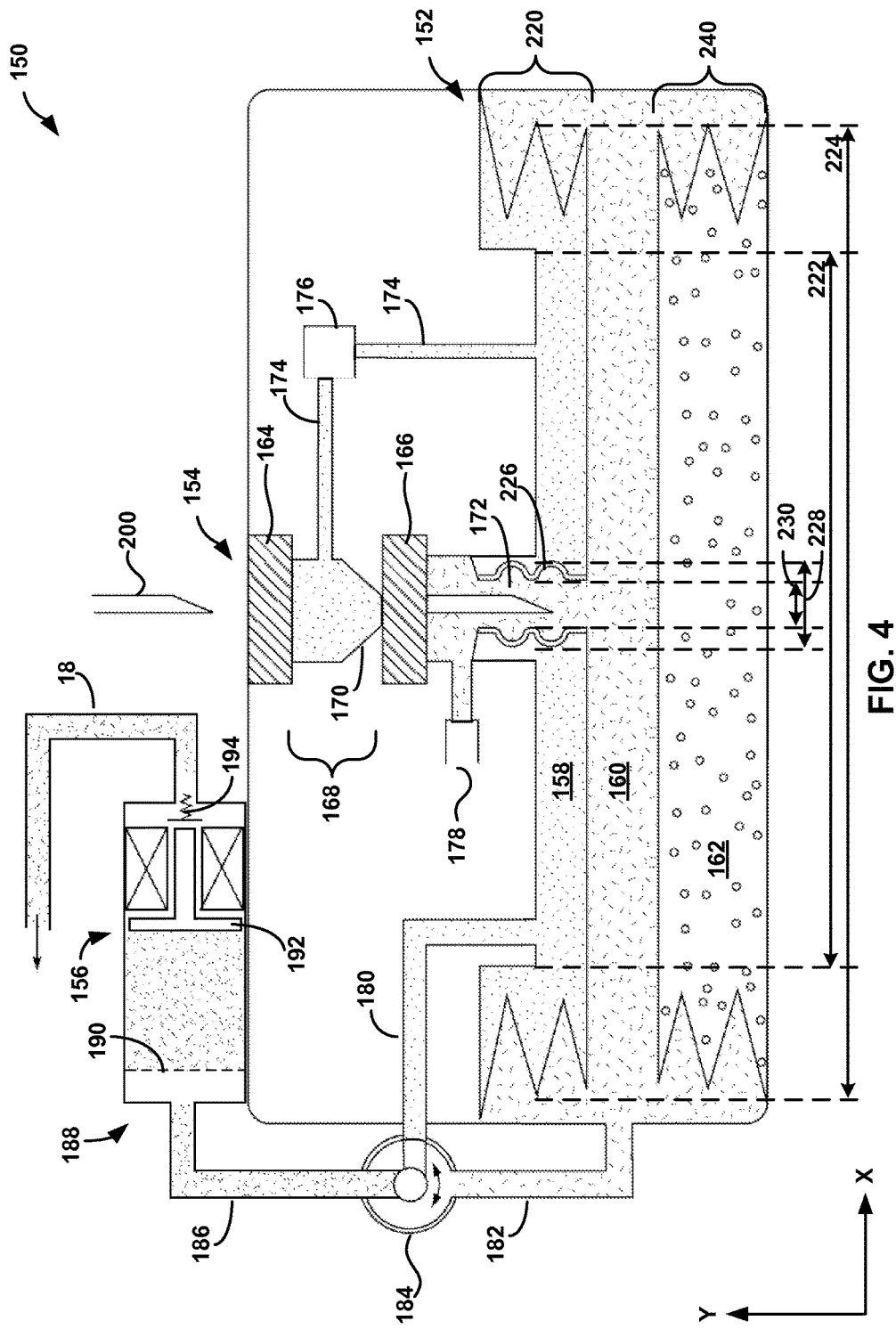
FIG. 4 is a conceptual diagram illustrating an example refill inlet port and reservoir arrangement for an example implantable fluid delivery device.

FIG. 4 is a conceptual diagram illustrating various components of an example IMD 150. IMD 150 may be implanted in patient 16 in addition to, or in lieu of, IMD 12. IMD 150 may correspond substantially to IMD 12 (FIGS. 1 and 2) and may include additional components illustrated and described with respect to IMD 12. IMD 150 may also communicate with programmer 20 (FIGS. 1 and 3) or another external device communicatively coupled to IMD 150. IMD 150 includes reservoir unit 152, inlet port 154 and fluid delivery pump 156. Reservoir unit 152 includes first fluid reservoir 158, second fluid reservoir 160 and propellant reservoir 162. IMD 150 is refilled through inlet port 154, which includes first septum 164, second septum 166, fluid intake aperture 168, and fluid intake aperture restrictor 170. Fluid pathway 172 allows fluid communication between second septum 166 and second fluid reservoir 160. Fluid intake aperture 168 is in fluid communication with first fluid reservoir 158 through fluid pathways 174. Sensors 176 and 178 communicate with fluid pathways 174 and 172, respectively. Fluid exits first fluid reservoir 158 for delivery through fluid delivery pump 156 via fluid pathway 180 and valve 184. Similarly, fluid exits second fluid reservoir 160 via fluid pathway 182 and valve 184. Valve 184 connects to mixing chamber 188 through fluid pathway 186. Mixing chamber 188 is fluidly connected to fluid delivery pump 156 and includes filter 190. Fluid delivery pump 156 includes piston 192 to generate pressure to force fluid through valve 194 and into catheter 18.

In general, the components and operation of IMD 150 may correspond to the description of the components and operation of IMD 12 (FIGS. 1 and 2). For example, fluid is added and withdrawn from IMD 150 through inlet port 154 using fluid delivery needle 200, e.g., percutaneously inserted into patient 16. Fluid delivery needle 200 is traversed in the Y-direction indicated on FIG. 4 to penetrate first septum 164. In some examples, IMD 150 includes a sensor configured to detect needle 200 penetrating first septum 164, e.g., for communication to programmer 20. In some examples, septum penetration is detected based on tactile response, e.g., physical pressure required to pierce first septum 164. In either case, a tip of needle 200 resides in fluid intake aperture 168 defined by inlet port 154 upon penetrating first septum 164 at a first depth. In some examples, fluid is added or withdrawn from first reservoir 158 through fluid intake aperture 168 and fluid pathways 174. In other examples, fluid delivery needle 200 continues to traverse in the Y-direction indicated on FIG. 4 to penetrate second septum 166 at a second depth. Again, penetration of second septum 166 may be detected in various ways including, e.g., with a sensor configured to detect needle penetration of second septum 166 or based on tactile response. Upon penetrating second septum 166, fluid may be added or withdrawn from second reservoir 160 through fluid pathway 172. In this manner, single inlet port 154 provides select fluid accessibility to both first reservoir 158 and second reservoir 160.

In general, user awareness of the position of fluid delivery needle 200 in IMD 150 is important to ensure that the user adds or withdraws fluid from an intended reservoir. In some examples, sensory techniques are utilized to identify a needle position within IMD 150. In other examples, however, IMD 150 is physically configured to prevent fluid delivery needle 200 from accessing the wrong reservoir. In one example, a cross-sectional area of inlet port 154 reduces between first septum 164 and second septum 166. For example, fluid intake aperture 168 includes fluid intake aperture restrictor 170, which functions to reduce the cross-sectional area of fluid intake aperture 168 as fluid intake aperture 168 extends from first septum 164 to second septum 166 (in the Y-direction indicated on FIG. 4). In the example of IMD 150, intake aperture restrictor 170 is a conical section of fluid intake aperture 170. In other examples, intake aperture restrictor 170 includes, e.g., an insert in inlet port 154 that reduces the cross-sectional area of inlet port 154. In any event, by reducing the cross-section area of inlet port 154, IMD 150 limits the size of fluid delivery needle 200 that can access second fluid reservoir 160. As a result, a large fluid delivery needle 200 that is used to refill first reservoir 158 cannot penetrate second septum 166. In various examples, inlet port 154 is configured to permit a fluid delivery needle larger than or equal to approximately 22 gauge (outer diameter (OD) 0.711 mm) to penetrate first septum 164 while blocking the needle from penetrating second septum 166. Inlet port 154 may be configured to permit a fluid delivery needle smaller than or equal to approximately 24 gauge (OD 0.559 mm) to penetrate second septum 166.

In general, first reservoir 158 and second reservoir 160 may be arranged in numerous locations within IMD 150 including, e.g., adjacent inlet port 154 (as shown in FIG. 4) or adjacent fluid delivery pump 192. In some examples, first reservoir 158 and second reservoir 160 are in a stacked arrangement (e.g., one on top of another) as in the example of FIG. 4. In other examples, first reservoir 158 and second reservoir 160 are in a coplanar arrangement (e.g., side-by-side) to minimize the overall thickness of IMD 150. In different examples, IMD 150 includes more than two reservoirs (e.g., three, four, five, or more reservoirs) and inlet port 154 includes more than two septa (e.g., three, four, five, or more septa) to provide additional flexibility for accessing different reservoirs and storing different fluids in different reservoirs.

In the example of FIG. 4, reservoir unit 152 is a three chamber bellows reservoir. Different bellows define first fluid reservoir 158 and propellant reservoir 162. Second fluid reservoir 160 is defined as the space between first fluid reservoir 158 and propellant reservoir 162. Propellant reservoir 162 biases against second fluid reservoir 160 in the Y-direction indicated in FIG. 4 to create positive pressure in second fluid reservoir 160, e.g., to convey fluid in second reservoir 160 to pump when valve 184 is opened. In turn, second fluid reservoir 160 biases against first fluid reservoir 158 to similarly create positive pressure in first reservoir 158. Propellant reservoir 162 houses a compressible gas that may include, but is not limited to, perfluoropentane, perfluorohexane, and combinations thereof. In some examples, propellant reservoir 162 surrounds both first reservoir 158 and second reservoir 160, e.g., to create pressure on a side wall of reservoir 158 and 160 extending in the Y-direction shown on FIG. 4. In some examples, propellant is placed in either first fluid reservoir 158 or second reservoir 160 and propellant reservoir 162 is configured to house a therapeutic fluid, e.g., by connecting fluid pathway 180 or 182 to propellant reservoir 162. In different examples, propellant reservoir 162 is replaced with a different biasing means including, e.g., a spring, hydraulic piston, or similar biasing means. In any event, a stacked bellows arrangement is not required for IMD 150. In general, first reservoir 158 and second reservoir 160 may be any component or set of components configured to house therapeutic fluid for delivery to patient 16.

Stacked bellows reservoir unit 152 allows first reservoir 158 and second reservoir 160 to house the same or different fluid amounts depending, e.g., on the anticipated delivery rates of different therapeutic fluids, the shelf-life of different therapeutic fluids, or to accommodate different therapeutic fluids during the service life of IMD 150. In some examples, reservoir unit 152 houses between approximately 5 milliliters and approximately 150 milliliters, such as between approximately 10 milliliters and approximately 60 milliliters. The fluid may be entirely housed in first reservoir 158, entirely housed in second reservoir 160, or divided between first reservoir 158 and second reservoir 160. As an example, reservoir unit 152 may house 150 milliliters. The 150 milliliters may be housed entirely in first reservoir 158 (e.g., with first reservoir 158 fully extended in the Y-direction) or entirely housed in second reservoir 160 (e.g., with first reservoir 158 fully collapsed in the Y-direction). Alternatively, the 150 milliliters may be split with, e.g., 75 milliliters in both first reservoir 158 and second reservoir 160, or 125 milliliters in first reservoir 158 and 25 milliliters in second reservoir 160. In any event, IMD 150 may house the same quantity or different quantities of fluid in first reservoir 158 and second reservoir 160.

First fluid reservoir 158 includes outer convolution 220 (e.g., the folded reservoir sidewall) that defines outer convolution outside diameter 224 and outer convolution inside diameter 222. Fluid reservoir 158 also includes inner convolution 226 that defines inner convolution outside diameter 228 and inner convolution inside diameter 230. In different examples, e.g., where fluid pathway 172 does not extend through fluid reservoir 158, first reservoir 158 does not include inner convolution 226. In the example of FIG. 4, propellant reservoir 162 includes an outer convolution 240 that defines convolution inner and outer diameters (not shown). In general, convolution diameters are selected based on a variety of factors including, e.g., the maximum capacity of first fluid reservoir 158 or propellant reservoir 162, the compliance of the material used to construct first fluid reservoir 158 or propellant reservoir 162, and to allow first fluid reservoir 158 or propellant reservoir 162 to expand and contract. In some examples, outer convolution outside diameter 224 is between approximately 25 millimeters and approximately 200 millimeters, such as between approximately 50 millimeters and approximately 80 millimeters. In some examples outer convolution inside diameter 222 is between approximately 20 millimeters and approximately 180 millimeters, such as between approximately 40 millimeters and approximately 70 millimeters. In some examples, inner convolution outside diameter 228 is between approximately 5 millimeters and approximately 20 millimeters, such as between approximately 7 millimeters and approximately 12 millimeters. In some examples, inner convolution inside diameter 230 is between approximately 3 millimeters and approximately 16 millimeters, such as between approximately 5 millimeters and approximately 10 millimeters. In some examples, the convolution inner diameter and outer diameter of convolution 240 are substantially similar to outer convolution outside diameter 222 and outer convolution inside diameter 224.

In general, reservoir unit 152, including first reservoir 158, second reservoir 160, and propellant reservoir 162 are constructed of materials that resist corrosion and degradation from, e.g., therapeutic fluids, propellant, and bodily fluids. Example materials include biocompatible metals, e.g., stainless steel, titanium, nitinol, or the like, biocompatible polymers, e.g., poly(ether ether ketone), silicone or silane based polymers, various elastomers, e.g., polyethylene, polypropylene, polystyrene, or the like. In one example, first reservoir 158 and propellant reservoir 162 are constructed of titanium. In another example, first reservoir 158 and/or propellant reservoir 162 are constructed of multiple materials. For example, outer convolution 220 and inner convolution 226 of first reservoir 158 may be constructed of different materials, e.g., to reduce the size of inner convolution 226 while achieving similar compliance between outer convolution 220 and inner convolution 226. In one example, outer convolution 220 is constructed of metal, e.g., titanium, while inner convolution 226 is constructed of an elastomer, e.g., ethylene propylene rubber, silicone rubber, fluorinated and perfluorinated elastomers, and the like.

IMD 150 includes valve 184, which is configured to control fluid communication between first reservoir 158, second reservoir 160, and fluid delivery pump 156. In some examples, valve 184 is configured to electromechanically actuate in response to instructions from a processor of IMD 150, or a processor of another device communicatively coupled to IMD 150. The processor can control valve 184 to selectively open and close fluid pathways 180 and 182, thereby allowing fluid delivery pump 156 to selectively draw fluid from either first reservoir 158 or second reservoir 160. Valve 184 may be any device that regulates fluid flow by opening, closing, or partially obstructing fluid pathway 180, 182, and 186. In some examples, IMD 150 includes multiple valves instead of a single valve 184, e.g., to prevent cross-contamination between fluid pathways 180 and 182. In one example, valve 184 is a three-way valve that regulates flow between fluid pathway 180, 182, and 186. In another example, valve 184 is a rotary valve in which rotation of valve openings functions to open and close access to attached fluid pathways 180, 182, and 186. In various examples, valve 184 may be a micro-machined valve, such as micro-machined diaphragm valve, ball valve, check valve, gate valve, slide valve, piston valve, rotary valve, shuttle valve, or the like. Valve 184 may include an actuator, such as a pneumatic actuator, electrical actuator, hydraulic actuator, or the like. In another example, valve 184 includes a solenoid, piezoelectric element, or similar feature to convent electrical energy into mechanical energy to mechanically open and close valve 184. Valve 184 may include a limit switch, proximity sensor, or other electromechanical device to provide confirmation that valve 184 is in an open or closed position.

During operation of IMD 150, fluid delivery pump 156 draws fluid from first reservoir 158 or second reservoir 160, e.g., according to a therapy program that specifies fluid delivery parameters, for delivery to patient 16. While the example of FIG. 4 includes a piston pump with piston 192, fluid delivery pump 156 may be any mechanism that delivers fluid from reservoirs 158, 160 to a therapy site within patient 16 including, e.g., the various fluid delivery pumps described above with respect to FIG. 2. In various examples, IMD 150 includes valve 194 interposed between the fluid discharge pathway of fluid delivery pump 156 and catheter 18. In one example, valve 194 is a controllable valve that actuates in response to instructions issued by a processor in IMD 150. In another example, valve 194 is a check valve, e.g., a one-way check valve that maintains head pressure on fluid delivery pump 156 and prevents reverse fluid flow from catheter 18 back into fluid delivery pump 156.

Because IMD 150 is configured to house multiple fluids, IMD 150 also facilitates substantially simultaneous delivery of multiple fluids to patient 16, e.g., according to a therapy program that specifies delivery of interleaved boluses of different fluids or according to a therapy program that specifies delivery of a mixed fluid based on two or more fluids housed within IMD 150. For example, to deliver interleaved fluid boluses from first reservoir 158 and second reservoir 160, valve 184 may actuate to open fluid pathway 180 during a backstroke of piston 192, resulting in fluid flow from first reservoir 158 to fluid delivery pump 156 in response to a vacuum generated by the backstroke of piston 192. During a subsequent backstroke of piston 192, valve 184 may actuate to close fluid pathway 180 and open fluid pathway 182, resulting in fluid flow from second reservoir 160 to fluid delivery pump 156. In this manner, IMD 150 may deliver interleaved boluses of different therapeutic fluids housed in first reservoir 158 and second reservoir 160. In some examples, IMD 150 draws fluid from first reservoir 158 for multiple strokes of piston 192 before actuating valve 184 to draw from second reservoir 160. In one example, IMD 150 draws substantially equal fluid volumes from first reservoir 158 and second reservoir 160 when delivering fluid boluses. For example, IMD 150 may draw from first reservoir 158 for two, three, four, or more strokes and then draw from second reservoir 160 for two, three, four, or more strokes. In another example, IMD 150 draws unequal fluid volumes from first reservoir 158 and second reservoir 160. For example IMD 150 may draw from first reservoir for two, three, four, or more strokes and then draw from second reservoir 160 for a single stroke.

In some examples, a therapy program specifies that a fluid mixture based on two or more fluids housed within IMD 150 be delivered to patient 16 through catheter 18. To facilitate mixing, IMD 150 includes mixing chamber 188 between valve 184 and fluid delivery pump 156. Mixing chamber 188 defines a cavity that allows different fluids drawn through fluid pathway 186 to combine and intermix before being pumped through fluid delivery pump 156 into catheter 18. In some examples, IMD 150 includes a defined mixing chamber 188, as illustrated in FIG. 4. In other examples, an inlet fluid pathway to fluid delivery pump 156 provides sufficient mixing space. As a result, IMD 150 may not include a defined mixing chamber 188.

Because external contaminants can enter IMD 150, e.g., by using an unclean needle or injecting a therapeutic fluid with an impurity, IMD 150 includes filter 190 in mixing chamber 188. Filter 190 helps block contaminants from reaching a target therapy delivery site in patient 16. Filter 190 is constructed of a material that is resistant to corrosion and degradation by therapeutic fluid. In various examples, filter 190 is sized to block particles less than or equal to approximately 0.50 micrometers, such as less than or equal to approximately 0.22 micrometers, or less than or equal to approximately 0.15 micrometers.

IMD 150 includes sensors 176 and 178 in communication with fluid pathways 174 and 178, respectively. Sensors 176 and 178 are communicatively coupled to a processor in IMD 150, e.g., for analysis and storage of measurement data captured by sensors 176 and 178. Sensors 176 and 178 may be arranged in a number of locations within IMD 150 including, e.g., in fluid pathway 174 adjacent to first septum 164 and in fluid pathway 172 adjacent to second septum 166. In general, sensors 176 and 178 are configured to measure a fluid characteristic within IMD 150 including, e.g., fluid flow rate, pressure, temperature electrolytic content, and the like.

In one example, sensors 176 and 178 are both pressure sensors. A pressure sensor may be any device capable of measuring pressure including, e.g., a capacitive pressure sensor, a piezo-electric pressure sensors, and a strain gauge pressure sensor. In some examples, when sensors 176 and 178 are pressure sensors, sensor 176 is configured to detect fluid delivery needle 200 penetrating into and/or withdrawing from first septum 164, while sensor 178 is configured to detect fluid delivery needle 200 penetrating into and/or withdrawing from second septum 166.

For example, a pressure wave (e.g., a pressure pulse) may propagate through fluid pathway 174 when fluid delivery needle 200 penetrates first septum 164 or is withdrawn from first septum 164. Similarly, a separate pressure wave may propagate through fluid pathway 172 when fluid delivery needle 200 penetrates second septum 166 or is withdrawn from second septum 166. Sensors 176 and 178 can be configured to detect the different pressure waves and, as a result, detect fluid delivery needle entry or withdrawal into a septum.

In various examples, IMD 150 may be configured to detect an electrical characteristic that changes when a fluid delivery needle penetrates a septum. IMD 150 may detect the electrical characteristic in conjunction with, or in lieu of, detecting pressure fluctuations when a fluid delivery needle penetrates a septum, as described above. FIG. 5A is a conceptual diagram illustrating an example inlet port 154 for IMD 150 that may be used to detect an electrical characteristic that varies when a fluid delivery needle penetrates a septum. Inlet port 154 is connected to first fluid reservoir 158 and second fluid reservoir 160, and includes previously described first septum 164, second septum 166, fluid intake aperture 168, fluid intake aperture restrictor 170, and fluid delivery needle 200. Inlet port 154 is installed within housing 250 of IMD 150 that includes needle guide 251. Inlet port 154 additionally includes first wire mesh layer 252, second wire mesh layer 254, third wire mesh layer 256, electrical connection port 258, sensor 260, resistor connection 261, resistor 262, ground connection 264, and O-ring 266. First septum 164 is interposed between first wire mesh layer 252 and second wire mesh layer 254. Third wire mesh layer 256 is disposed adjacent second septum 166 opposite fluid intake aperture 168. The configuration and operation of components illustrated in the example of FIG. 5A correspond to the description of like components in the example of FIG. 4.

In general, sensor 260 is configured to measure at least one electrical characteristic in IMD 150 including, e.g., current, voltage, or resistance. In one example, sensor 260 is an ohmmeter, i.e., a resistance meter. In another example, sensor 260 is a voltage meter. In different examples, IMD 150 includes multiple sensors, e.g., to measure different electrical characteristics or to measure an electrical characteristic in different locations. Sensor 260 is communicatively coupled to a processor in IMD 150 for, e.g., analysis and storage of measurement data. In some examples, data from sensor 260 are communicated to programmer 20, or another external device communicatively coupled to IMD 150, as described above with reference to FIG. 3.

First, second, and third wire mesh layers 252, 254, and 256 are layers of electrically conductive material that are penetrable by fluid delivery needle 200. First, second, and third wire mesh layers 252, 254, and 256 are configured to electrically connect to sensor 260 to detect a characteristic that varies when fluid delivery needle 200 is inserted or withdrawn through first septum 164 or second septum 166. Accordingly, first, second, and third wire mesh layers 252, 254, and 256 are constructed of an electrically conductive material that resists degradation from therapeutic and bodily fluids including, e.g., nickel, titanium, stainless steel, and alloys thereof, such as nitinol. In some examples, first and second wire mesh layers 252, 254 are molded into first septum 164 and/or third wire mesh layer 256 is molded into second septum 166. In other examples, first and second wire mesh layers 252, 254 are mechanically affixed to first septum 164 and/or third wire mesh layer 256 is mechanically affixed to second septum 166. A number of different items can be used to mechanically affix a wire mesh layer to a septum including, e.g., adhesive, clips, screws, staples, and the like. In one example, first wire mesh layer 252 is friction fit against first septum 164 with needle guide 252.

In the example of FIG. 5, first and second wire mesh layers 252, 254 are proximate first septum 164, and third wire mesh layer 256 is proximate second septum 166. In general, first and second wire mesh layers 252, 254 may be directly adjacent to first septum 164 and third wire mesh layer 256 directly adjacent to second septum 166, or at least one of first, second, or third wire mesh layers 252, 254, 256 may be disposed a distance away from first septum 164 and/or second septum 166, respectively. For example, second wire mesh layer 254 and/or third wire mesh layer 256 may be disposed a distance away from first septum 164 and/or second septum 166 (e.g., in the X-direction indicated on FIG. 5A). A separation distance between a wire mesh layer and a bottom surface of a septum may prevent electrical contact between the wire mesh layer and a fluid delivery needle until the fluid delivery needle is inserted to a depth where the septum is penetrated, e.g., thereby placing the fluid delivery needle in fluid communication with a reservoir. By contrast, without a separation distance between a septum and a wire mesh layer, electrical contact may be established when a fluid delivery needle is first inserted into the septum without fully penetrating the septum. In some examples, second wire mesh layer 254 may be disposed away from first septum 164 and/or third wire mesh layer 256 may be disposed away from second septum 166 by a distance between approximately 0.05 inches and approximately 0.25 inches, such as, e.g., between approximately 0.10 inches and approximately 0.175 inches. According to one example, second wire mesh layer 254 and/or third wire mesh layer 256 may be disposed away from first septum 164 and/or second septum 166 by a distance of approximately 0.13 inches. Regardless of how a wire mesh layer is configured relative to a septum, in IMD 150, first, second, and third wire mesh layers 252, 254, and 256 are configured to be penetrated by fluid delivery needle 200.

In some examples, first, second, and third wire mesh layers 252, 254, and 256 include mesh openings that allow fluid delivery needle 200 to pass through the openings while also producing electrical contact between at least one mesh opening and fluid delivery needle 200. According to some examples, mesh openings may be substantially equivalent to an outer diameter of fluid delivery needle 200 including, e.g., the example needle sizes discussed with reference to FIG. 4.

As described, IMD 150 and, in particular inlet port 154, may be configured to detect an electrical characteristic that changes when fluid delivery needle 200 penetrates a septum. FIG. 5B is an equivalent circuit diagram for inlet port 154 of FIG. 5A, where like reference numerals indicate like components. Before fluid delivery needle 200 is inserted into IMD 150, inlet port 154 is configured as an open circuit. First wire mesh layer 252 is electrically connected to sensor 260 through needle guide 251, housing 250 and ground connection 264. Second wire mesh layer 254 and third wire mesh layer 256 are electrically connected through resistor connection 261, which includes resistor 262. Sensor 260 is electrically connected to resistor connection 261 through electrical connection port 258, e.g., with wiring that extends through electrical connection port 258. Upon inserting fluid delivery needle 200 (which is generally constructed of an electrically conductive material or which generally includes a conductive coating) through first septum 164, a circuit is closed. The circuit includes: sensor 260, ground connection 264, housing 250, needle guide 251, first wire mesh layer 252, fluid delivery needle 200, second wire mesh layer 254, and resistor connection 261 with resistor 262. Sensor 260 measures an electrical characteristic, e.g., resistance, across the closed circuit to detect, e.g., when fluid delivery needle 200 penetrates first septum 164, whether fluid delivery needle 200 continues to penetrate first septum 164, or when fluid delivery needle 200 is withdrawn from first septum 164. For example, sensor 260 may sense a resistance substantially equivalent to the resistance of resistor 262, plus any resistance associated with wire mesh layers 252, 254, needle 200, and associated electrical interconnections. Upon penetration of needle through layer 252 and layer 254, the circuit is closed such that the resistance drops from an open circuit condition to a lower resistance, which may correspond to the resistance of resistor 262.

Upon further inserting fluid delivery needle 200 through second septum 166, a second, parallel circuit is closed. The circuit includes: sensor 260, ground connection 264, housing 250, needle guide 251, first wire mesh layer 252, fluid delivery needle 200, and third wire mesh layer 256. Again, sensor 260 measures an electrical characteristic, e.g., resistance, across the second closed circuit to detect, e.g., when fluid delivery needle 200 penetrates second septum 166, whether fluid delivery needle 200 continues to penetrate second septum 166, or when fluid delivery needle 200 is withdrawn from second septum 166. In some examples, sensor 260 measures a decreased resistance value when fluid delivery needle 200 contacts third wire mesh layer 256 as compared to when fluid delivery needle 200 only contacts first wire mesh layer 252 and second wire mesh layer 254. In particular, the needle 200 couples first wire mesh layer 252 and second wire mesh layer 254 to third wire mesh layer 256, providing a short circuit bypass of resistor 262. Consequently, sensor 260 detects an abrupt drop in resistance from the previous resistance value, indicating that the third wire mesh layer 256 has been contacted by needle 200, and, in turn, indicating that the needle has penetrated through second septum 166. In this manner, IMD 150, and in particular inlet port 154, is configured to detect an electrical characteristic that varies when fluid delivery needle 200 penetrates either first septum 164 or second septum 166. In addition, as described in greater detail with reference to FIGS. 2 and 3 above, IMD 150 may send sensor data to programmer 20, or another device communicatively coupled to IMD 150, to provide a user with periodic or real-time information indicating the position of fluid delivery needle 200. Thus, the user is aware of the position of fluid delivery needle 200 to ensure that fluid is being added or withdrawn from the appropriate reservoir.

While the example of FIGS. 5A and 5B include one inlet port configuration for detecting an electrical characteristic that varies as fluid delivery needle 200 penetrates either first septum 164 or second septum 166, IMD 150 may be configured in any general arrangement to electrically detect penetration of fluid delivery needle 200. In one example, inlet port 154 is configured as a closed circuit and penetration by fluid delivery needle 200 breaks the circuit, thereby allowing sensor 260 to detect penetration of first septum 164 by fluid delivery needle 200. In another example, second septum 166 includes two wire mesh layers while first septum 164 only include a single wire mesh layer, reversing the electrical configuration of first septum 164 and second septum 166 in the example of FIGS. 5A and 5B. In a further example, first septum 164 and second septum 166 each include two wire mesh layers, e.g., connected to separate sensors, allowing different electrical characteristics to be separately detected over first septum 164 and second septum 166.

In some examples, inlet port 154 is configured as a modular unit that may be inserted into a separate housing 250 of IMD 150. In these examples, o-ring 266 functions, e.g., to block fluid exchange between module inlet port 154 and patient 16, and to increase the friction fit between housing 250 and inlet port 154. To accommodate electrical connections and fluid pathways, inlet port 154 may include various additional ports to facilitate connections between housing 250 and inlet port 154. In one example, inlet port 154 includes electrical connection port 258, which allows an electrical connection (e.g., wiring) to extend between inlet port 154 and sensor 260. In some examples, inlet port 154 includes additional ports (not shown) for connecting first fluid reservoir 158 and second fluid reservoir 160 to inlet port 154. The various connection ports, including electrical connection port 258, may be referred to as hermetic feedthrough connections. In general, inlet port 154 and housing 250 are constructed of biocompatible materials that resist corrosion to bodily and therapeutic fluids. In some examples, housing 250 and needle guide 251 are constructed of a biocompatible electrically conductive material, e.g., stainless steel, titanium. In some examples, inlet port 154 is constructed of a biocompatible polymeric material, e.g., poly(ether ether ketone) (PEEK), that provides compliance and electrical isolation when inlet port 154 is inserted into housing 250.

In another example according to this disclosure, etched or otherwise machined discs may be employed instead of wire meshes as the means by which sensor 260 measures at least one electrical characteristic in IMD 150 including, e.g., current, voltage, or resistance to detect a needle passing through one or more of septum 164 or septum 166. In some cases, a combination of two or more etched or otherwise machined discs may function in much the same way as the wire mesh, e.g. IMD 150 may be configured to detect an electrical characteristic that changes when a fluid delivery needle penetrates slots machined in the discs. However, such discs may be simpler and less expensive to manufacture than wire meshes. Thus, in some examples, IMD 150 may employ one or more sets of stacked discs, e.g. in addition to or in lieu of one or more of first wire mesh layer 252, second wire mesh layer 254, or third wire mesh layer 256 in the example of FIGS. 5A and 5B.

Figure 8A:
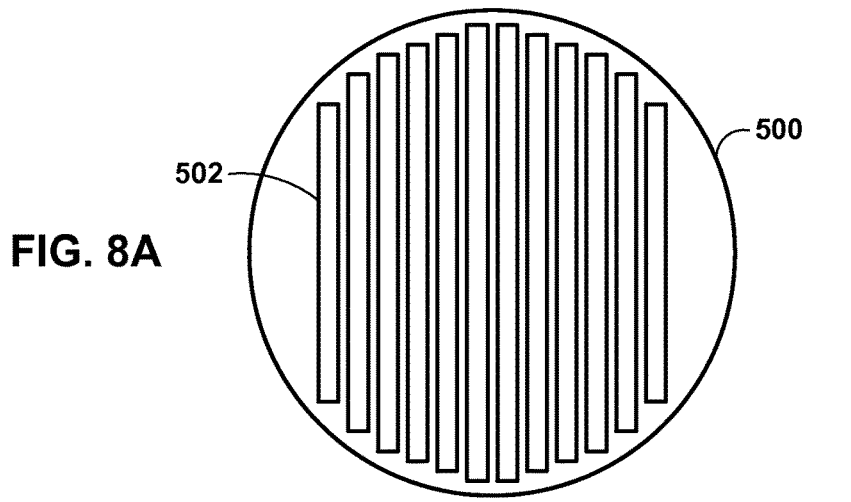
FIGS. 8A-8C illustrate a number of examples of stacked discs for use in an inlet port of an implantable fluid deliver device.
Figure 8B:
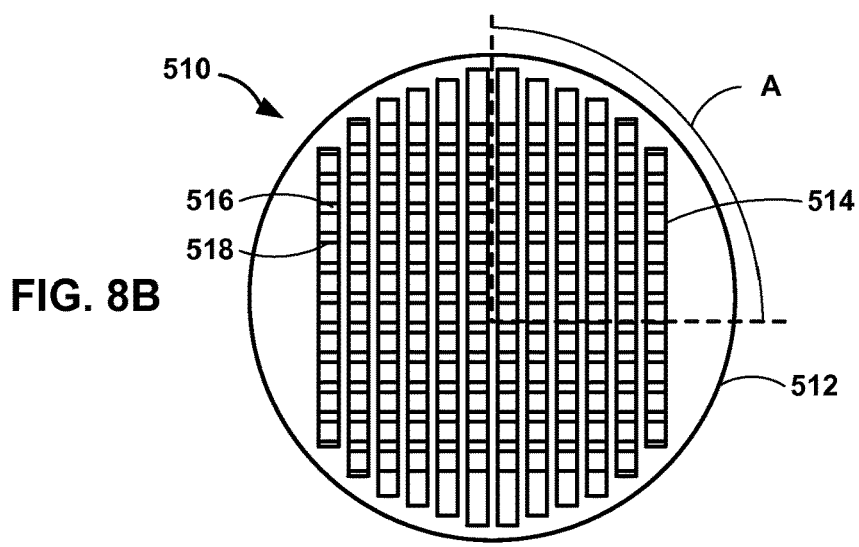
Figure 8C:
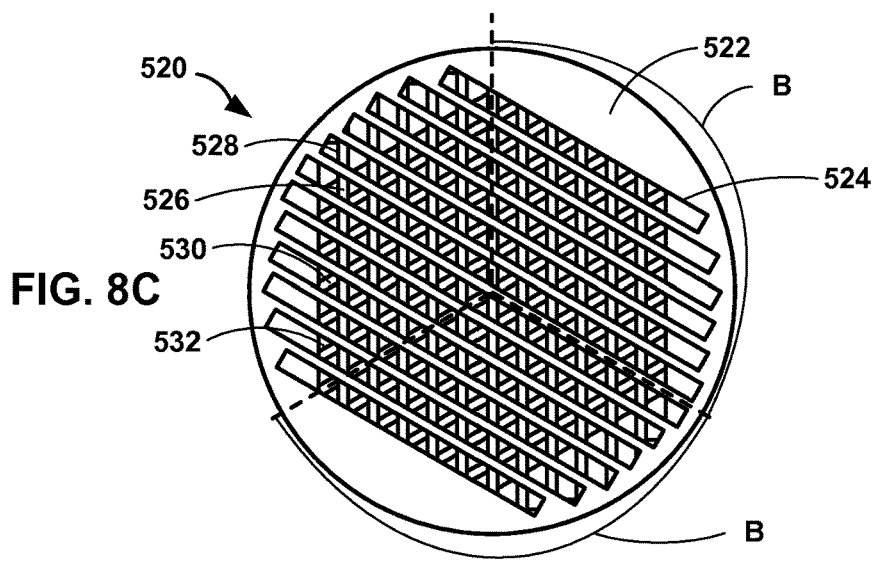

FIGS. 8A-8C illustrate several examples including a number of discs, which may be stacked to create a mesh through which a fluid delivery needle may be passed. FIG. 8A is a plan view of an example disc 500, including a plurality of parallel slots 502. Disc 500 may be manufactured from an electrically conductive material that resists degradation from therapeutic and bodily fluids including, e.g., nickel, titanium, stainless steel, and alloys thereof, such as nitinol. In the example of FIG. 8A, slots 502 are arranged generally parallel with respect to one another and span a majority of the surface area of disc 500. The size and spacing between slots 502 may vary depending on, among other factors, the size of the fluid delivery needle that is intended to penetrate a set of stacked discs in accordance with this disclosure. Slots 502 may be machined in disc 500 employing a number of material removal processes, including, e.g. machining, etching, laser or liquid cutting, electrical discharge machining (EDM), and the like.

FIGS. 8B and 8C illustrate two examples of sets of stacked discs similar to disc 500 of FIG. 8A, either or both of which may be employed in conjunction with sensor 260 in a manner similar to that described above with reference to wire mesh layers 252-256 of FIGS. 5A and 5B. FIG. 8B illustrates an example including a set 510 of two staked discs and FIG. 8C illustrates an example including a set 520 of three stacked discs.

In FIG. 8B, discs 512 and 516 are stacked such that slots 514 and 518, respectively, are arranged at an angle A to one another. In the example of FIG. 8B, angle A is approximately equal to 90 degrees such that the apertures formed by the intersection of slots 514 and 518 of discs 512 and 516, respectively, are generally rectangular and sized according to the width of and spacing between the slots.

In FIG. 8C, discs 522, 526, and 530 are stacked such that slots 524, 528, and 532, respectively, are arranged at an angle B to one another. In the example of FIG. 8C, angle B is approximately equal to 120 degrees such that the apertures formed by the intersection of slots 524, 528, and 532 of discs 522, 526, and 530, respectively, are generally triangular and sized according to the width of and spacing between the slots. In other examples, more than three discs may be stacked together to form apertures through which a fluid delivery needle may be passed. In addition, the size, spacing, and shape of the slots machined into the stacked discs may vary depending on, e.g., the size and shape of the fluid delivery needle intended to penetrate the stack.

Either of the example sets 510 or 520 of stacked discs of FIGS. 8B and 8C may be arranged and employed in an IMD, e.g. IMD 150 in a manner substantially similar to that described above with reference to first, second, and third wire mesh layers 252, 254, and 256 of FIGS. 5A and 5B. For example, sets 510 or 520 of stacked discs may be configured such that the apertures formed by the slots of the respective discs allow fluid delivery needle 200 to pass through the openings while also producing electrical contact between at least one aperture in the stack of discs and fluid delivery needle 200. According to some examples, the apertures in sets 510 or 520 of stacked discs may be substantially equivalent to an outer diameter of fluid delivery needle 200 including, e.g., the example needle sizes discussed with reference to FIG. 4. As described above, sets 510 or 520 of stacked discs may be arranged with respect to one or more of septa 164 or 166 such that penetrating the stacked discs with fluid delivery needle 200 changes an electrical characteristic sensed by sensor 260 and indicates that the needle has penetrated and/or passed through one of the septa.

In one example, the discs described with reference to FIGS. 8A-8C may be fabricated from steel, Titanium (Ti) or a Titanium alloy, including, e.g. an American Society for Testing and Materials (ASTM) grade 5 Titanium or Nitinol (NiTi). A disc such as those described above may include a tensile strength in a range from approximately 80 to approximately 300 kilopounds per square inch (ksi) (552-2068 megapascals), a yield strength in a range from approximately 10 to approximately 120 ksi (69-827 MPa), and an elongation to failure in a range from approximately 10% to approximately 50%. In one example, a disc in accordance with this disclosure includes a tensile strength in a range from approximately 80 to approximately 160 ksi (552-1103 megapascals), a yield strength in a range from approximately 40 to approximately 120 ksi (276-827 MPa), and an elongation to failure in a range from approximately 20% to approximately 50%. In one example, a disc is fabricated from 316 stainless steel with a tensile strength approximately equal to 81 ksi (558 MPa), yield strength approximately equal to 42 ksi (290 MPa), an elongation to failure approximately equal to 50%, and a modulus of elasticity of approximately $28 \times 10^6$ psi (193 gigapascals). In another example, a disc is fabricated from ASTM grade 5 titanium alloy (Ti-6Al-4V) with a tensile strength approximately equal to 130 ksi (828 MPa), yield strength approximately equal to 120 ksi (759 MPa), an elongation to failure approximately equal to 10%, and a modulus of elasticity of approximately $16.3 \times 10^6$ psi (112 GPa). In another example, a disc is fabricated from Nitinol with a tensile strength in a range from approximately 130 to approximately 275 ksi (896-1896 MPa), yield strength in a range from approximately to 10 to approximately 120 ksi (69-827 MPa), an elongation to failure in a range from approximately to 5% to approximately 50%, and a modulus of elasticity in a range from approximately $4 \times 10^6$ to approximately $12 \times 10^6$ psi (27.5-82.7 GPa).

As noted above, discs such as those described above may be shaped and sized depending on, among other factors, the size of the fluid delivery needle that is intended to penetrate a set of stacked discs in accordance with this disclosure. In one example, a disc includes a generally circular shape including a diameter in a range from approximately 0.4 to approximately 0.6 inches (10.2-15.2 millimeters), a thickness in a range from approximately 0.002 to approximately 0.005 inches (0.051-0.127 mm), slot widths in a range from approximately 0.02 to approximately 0.05 inches (0.51-1.27 mm), and spacing between slots in a range from approximately 0.01 to approximately 0.03 inches (0.25-0.76 mm).

With further reference to FIG. 4, IMD 150 in the example of FIG. 4 includes valve 184. In different examples, IMD 150 includes multiple valves instead of a single valve 184 to control fluid conveyance between first reservoir 158, second reservoir 160 and fluid delivery pump 156. FIG. 6 is a functional block diagram of an alternative example reservoir outlet valve configuration for IMD 150, which includes first fluid reservoir 158, second fluid reservoir 160, first reservoir discharge valve 280, second reservoir discharge valve 282, fluid pathways 180, 182, and 186, fluid delivery pump 156, piston 192, and valve 194. Fluid pathway 180 fluidly connects first fluid reservoir 158 to fluid delivery pump 156 through first reservoir discharge valve 280 and fluid pathway 186. Fluid pathway 182 fluidly connects second fluid reservoir 160 to fluid delivery pump 156 through second reservoir discharge valve 282 and fluid pathway 186. In general, the configuration and operation of components illustrated in the example of FIG. 6 correspond to the description of like components in the example of FIG. 4.

In some examples, first and second reservoir discharge valves 280 and 282 may be the same as valve 184, discussed above with respect to FIG. 4. In one example, first and second reservoir discharge valves 280 and 282 are both communicatively coupled to a processor in IMD 150 that controllably actuates both first reservoir discharge valve 280 and second reservoir discharge valve 282 to control fluid delivery from first and second fluid reservoirs 158 and 160 to fluid delivery pump 156. In this example, valves 280 and 282 may be a solenoid valve, a valve with a pneumatic actuator, electrical actuator, hydraulic actuator, or similar valve that is configured to actuate in response to instructions from a processor in IMD 150.

In further examples, first and second reservoir discharge valves 280 and 282 may be passive valves. A passive valve is a valve that is not coupled to a processor in IMD 150 for controllable actuation. In these examples, first and second reservoir discharge valves 280 and 282 may actuate, e.g., based on different hydrodynamic forces within IMD 150. In one example, first and second reservoir discharge valves 280 and 282 are check valves that have different opening pressures, and, as a result, respond differently to different hydrodynamic forces within IMD 150.

As noted, a check valve may function as a passive valve in some examples. Different types of check valves suitable for first and second reservoir discharge valves 280 and 282 include, e.g., but not limited to, flat, spherical, conical, flapper, and duckbill check valves. In some examples, a moving portion of a passive check valve may be constructed of an elastomeric material (e.g., entirely or with an elastomeric coating) and biased against a comparatively rigid valve seat. In additional examples, a moving portion of a passive valve may be constructed of a comparatively rigid material and biased against an elastomeric valve seat. In either set of examples, a mechanical seal is established when the passive valve is closed. Example elastomers that may be used in a passive valve include, but are not limited to, ethylene propylene rubber, silicone rubber, fluorinated and perfluorinated elastomers, and the like. Examples of rigid materials that may be used in a passive check valve include, but are not limited to, biocompatible metals, such as titanium, stainless steel, nickel, cobalt, and combinations thereof. In general, a spring may provide a biasing force for a check valve. A check valve spring may be constructed of a biocompatible metal including, e.g., titanium, stainless steel, nickel, cobalt, and combinations thereof, such as a MP35N® superalloy. According to one example, a check valve may comprise a flat titanium valve with a perfluorinated elastomeric coating that is biased against a flat titanium seat by a spring constructed of a MP35N alloy.

In a different example, first reservoir discharge valve 280 is a passive valve while second reservoir discharge valve 282 is a controllable valve communicatively coupled to a processor in IMD 150. Examples of passive valves and controllable valves are described above. According to one example, first reservoir discharge valve 280 is a check valve while second reservoir discharge valve 282 is a solenoid valve. First reservoir discharge valve 280 may have an opening pressure between approximately 0.25 pounds per square inch (1724 pascals) and approximately 5.0 pounds per square inch (34475 pascals), such as approximately 2.0 pounds per square inch (13790 pascals). Second reservoir discharge valve 282 is normally closed (i.e., requires actuation to open). During operation of IMD 150 to deliver therapeutic fluid to patient 16, fluid delivery pump 156 generates a vacuum in fluid pathway 186, opening first reservoir discharge valve 280 while second reservoir discharge valve 282 remains closed. Fluid delivery pump 156 draws fluid from first fluid reservoir 158 when first reservoir discharge valve 280 opens.

Alternatively, to draw fluid from second fluid reservoir 160, a processor in IMD 150 issues instructions for second reservoir discharge valve 282 to actuate open. Fluid delivery pump 156 freely draws fluid from second fluid reservoir 160 and thus does not generate sufficient vacuum to open first reservoir discharge valve 280. In this manner, IMD 150 selectively draws fluid from either first fluid reservoir 158 or second fluid reservoir 160 for delivery to patient 16. Using a passive valve and controllable valve in combination may reduce the operating energy requirements of IMD 150, e.g., because IMD 150 does not consume energy to repeatedly actuate first reservoir discharge valve 280. In some examples, energy savings are enhanced when IMD 150 is used with a therapy program that preferentially draws fluid from first fluid reservoir 158, e.g., where first fluid reservoir 158 is configured as a primary reservoir.

Figure 7:
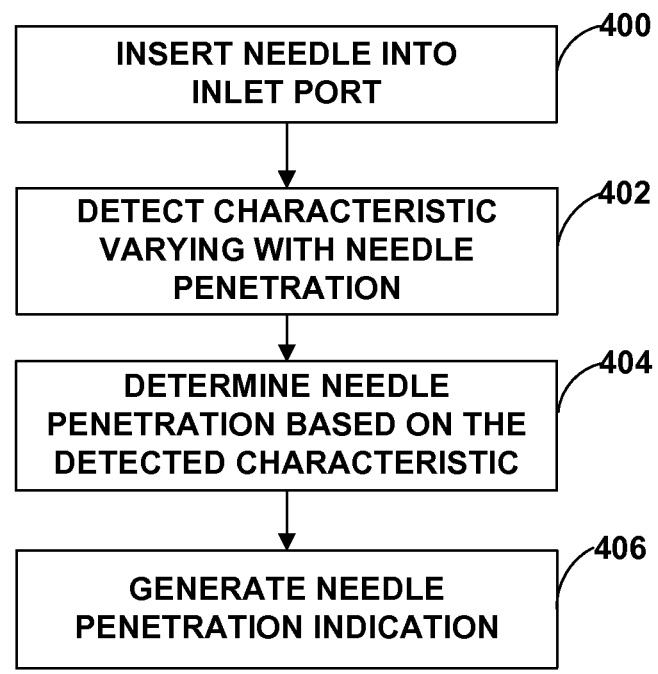
FIG. 7 is a flow chart of an example method of accessing a fluid reservoir of an example fluid delivery device.

FIG. 7 is a flow chart of an example method of accessing a fluid reservoir of an example fluid delivery device. In particular, FIG. 7 illustrates an example method for accessing an inlet port of an IMD that houses multiple reservoirs, where each reservoir is in fluid communication with a single inlet port that is configured to detect entry of a fluid delivery needle into the inlet port. The method of FIG. 7 includes inserting a fluid delivery needle into an inlet port (400) and detecting a characteristic that varies as the fluid delivery needle penetrates a septum (402). Again, in some examples, the characteristic may be any of a variety of pressure or electrical characteristics. The method of FIG. 7 also includes determining when the fluid delivery needle penetrates the septum based on the detected characteristic (404) and generating a needle penetration indication (406).

As described above with respect to FIGS. 2, 4, 5A, and 5B, a fluid delivery needle, e.g., a hypodermic needle, may be inserted into an inlet port of a fluid delivery device (400). In some examples, the fluid delivery needle is percutaneously inserted when the fluid delivery device is implanted in the body of a patient. The inlet port resides on a peripheral surface of a housing of the fluid delivery device and is configured to fluidly communicate with a reservoir within the fluid delivery device. In some examples, the fluid delivery device includes multiple reservoirs, and each reservoir is in fluid communication with the same inlet port. In general, the inlet port includes a septum, e.g., to seal the inlet port and to prevent unwanted fluid communication between the fluid delivery device and the body of the patient. The fluid delivery device may include multiple septa, e.g., in a stacked arrangement, to provide access to different reservoirs that are each connected to the same inlet port. Inserting the fluid delivery needle into the inlet port results in the fluid delivery needle penetrating a first septum, e.g., placing the fluid delivery needle in fluid communication with a first reservoir. In some examples, inserting the fluid delivery needle further into the inlet port results in the fluid delivery needle penetrating a second septum in addition to penetrating the first septum, e.g., closing fluid communication between the fluid delivery needle and the first reservoir while placing the fluid delivery needle in fluid communication with a second reservoir.

The method of FIG. 7 includes detecting a characteristic that varies as the fluid delivery needle penetrates a septum (402). In different examples, the fluid delivery device includes one or more sensors configured to detect a characteristic that varies as the fluid delivery penetrates a septum. In one example, a septum includes an electrically conductive material and a sensor in the fluid delivery device is configured to detect an electrical characteristic that changes when the fluid delivery needle penetrates a septum. In various examples, the electrical characteristic is voltage, current, or resistance. In another example, the fluid delivery device includes a pressure sensor, e.g., in a fluid pathway connecting the inlet port to a reservoir. The pressure sensor is configured to detect a pressure pulse, e.g., propagating through fluid extending between the penetrated septum and the sensor. Regardless of the number, type, or location of the sensor, the sensor is communicatively coupled to a processor. In one example, the processor executes instructions that cause the sensor to detect the characteristic that varies when a fluid delivery needle penetrates the septum. In some examples, the processor executes instructions that cause the sensor to continuously detect the characteristic. In other examples, the processor executes instructions that cause the sensor to intermittently or selectively detect the characteristic, e.g., upon receiving instructions that a user intends to insert a fluid delivery needle into an inlet port (400). In some examples, the sensor automatically sends sensor data to the processor, e.g., for analysis and storage on memory.

Upon detecting a characteristic that varies when a fluid delivery needle penetrates a septum (402), the method of FIG. 7 also includes determining when the fluid delivery needle penetrates the septum based on the detected characteristic (404). In general, a processor of the fluid delivery device, or the processor of another device communicatively coupled to the fluid delivery device, analyzes the detected characteristic to determine if the fluid delivery needle penetrated a septum. In some examples, the processor determines that a fluid delivery needle penetrated a septum by comparing new values for the detected characteristic (e.g., after penetration) to previously established values for the detected characteristic (e.g., before penetration), which, in some examples, are stored on memory. Previously established values may be reference values, e.g., values established independent of the operation of the IMD, or values previously measured by the IMD. A change in the detected characteristic, e.g., pressure, resistance, voltage, current, or the like, between the new and previously established values indicates that the fluid delivery needle penetrated the septum.

In further examples, the processor determines that the fluid delivery needle penetrated the septum by comparing values for the detected characteristic to an absolute value, e.g., stored in a look-up table in memory. If values for the detected characteristic are, e.g., above, below, or equal to the absolute valve stored in memory, the processor determines that the fluid delivery needle penetrated the septum. In some examples, the processor distinguishes when the fluid delivery needle penetrates one septum, e.g., a first septum, from when the fluid delivery needle penetrates another septum, e.g., a second septum. In one example, the processor receives values for the detected characteristic from different sensors to distinguish when the fluid delivery needle penetrates different septa. In another example, the values from the same sensor change as the fluid delivery needle penetrates different septa, allowing the processor to distinguish when the fluid delivery needle penetrates different septa. In some examples, after the processor determines that the fluid delivery needle penetrated one septum, the processor compares values for the detected characteristic to different data, e.g., a different look-up table in memory, to determine when the fluid delivery needle penetrates a different septum.

The method of FIG. 7 also includes generating a needle penetration indication (406). In general, the fluid delivery device is communicatively coupled to an external device such a programmer. In some examples, a processor of the fluid delivery device determines when a fluid delivery needle penetrates a septum and communicates the determination, e.g., via a telemetry module, to the external device. In other examples, a processor of the external device receives information, e.g., values for the detected characteristic, and determines when the fluid delivery needle penetrates the septum. In either set of examples, the processor of external device may generate a needle penetration indication (406) when septum penetration is determined. In various examples, the needle penetration indication may include an audible sound, a tactile indication (e.g., vibration), a visual indication, and combinations thereof. In some examples, different needle penetration indications are issued when different septa are penetrated. In this manner, the method of FIG. 7 may provide a user with septum awareness to help the user access a desired fluid reservoir in the fluid delivery device. Further, septum awareness may help a user know when it is safe or appropriate to actuate a syringe to deliver a fluid.

While not shown in the example of FIG. 7, the method of FIG. 7 can be repeated to detect fluid delivery needle withdrawal from the fluid delivery device. In some examples, the fluid delivery needle will be intentionally withdrawn from the fluid delivery device. In other examples, the fluid delivery needle may be accidently withdrawn, e.g., entirely out of the fluid delivery device or through a septum to placing the fluid delivery needle in fluid communication with a different reservoir. In either situation, a sensor may detect a characteristic that varies when a fluid delivery needle is withdrawn from a septum, which may be the same characteristic and may be detected in a like manner as the characteristic that varies when a fluid delivery needle is inserted into the septum, as discussed above. Further, a processor may determine when the fluid delivery needle is withdrawn from the septum based on the detected characteristic, e.g., according to a similar procedure outlined for determining when a fluid delivery needle penetrates a septum. A needle withdrawal indication may then be provided to a user. In some examples, the needle withdrawal indication is different than the needle penetration indication. In some examples, the needle withdrawal indication varies, e.g., based on the specific septum from which the needle was withdrawn.

In general, the foregoing examples describe fluid delivery devices that include multiple reservoirs that are each accessible through the same inlet port. In some examples, the fluid delivery devices were configured to detect a fluid delivery needle penetrating a septum. In some examples, each reservoir in the fluid delivery devices included separate discharge valves between a reservoir and a fluid delivery pump. While described together in various examples, it should be appreciated that the concepts of this disclosure can be altered as will be appreciated by those of skill in the art. As one example, the fluid delivery needle detection concepts of this disclosure can be employed in a device with a single septum, e.g., a fluid delivery device with a single fluid reservoir, in addition to being employed in a fluid deliver device with multiple septa. As another example, the reservoir discharge valve concepts of this disclosure can be employed in a device where each reservoir is accessible through a separate inlet port in addition to being employed in a fluid delivery device where multiple reservoirs are accessible through a single inlet port. These as well as other examples are within the scope of the disclosure.

Further, although the target therapy delivery site described with reference to the foregoing examples is proximate to the spinal cord of a patient, other applications of therapy systems in accordance with this disclosure include alternative delivery sites. In some examples, the target delivery site may be proximate to different types of tissues including, e.g., nerves, e.g. sacral, pudendal or perineal nerves, organs, muscles or muscle groups. In one example, a catheter may be positioned to deliver a therapeutic fluid to a deep brain site or within the heart or blood vessels. Delivery of a therapeutic fluid within the brain may help manage a number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. A catheter may also be positioned to deliver insulin to a patient with diabetes. In other examples, the system may deliver a therapeutic fluid to various sites within a patient to facilitate other therapies and to manage other conditions including peripheral neuropathy or post-operative pain mitigation, ilioinguinal nerve therapy, intercostal nerve therapy, gastric drug induced stimulation for the treatment of gastric motility disorders and/or obesity, and muscle stimulation, or for mitigation of peripheral and localized pain e.g., leg pain or back pain.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A therapeutic fluid delivery system comprising:
a first reservoir configured to house a first therapeutic fluid;
a second reservoir configured to house a second therapeutic fluid;
an inlet port configured to receive a first fluid delivery needle having a first diameter and a second fluid delivery needle having a second diameter less than the first diameter, wherein the inlet port comprises a first septum and a second septum, and
wherein the inlet port is configured for fluid communication between the first fluid delivery needle and the first reservoir when the first fluid delivery needle penetrates the first septum but not the second septum, and the inlet port is further configured for fluid communication between the second fluid delivery needle and the second reservoir when the second fluid delivery needle penetrates both the first septum and the second septum; and
wherein the inlet port exhibits a reduced cross-sectional area between the first septum and the second septum such that the second needle exhibiting the second diameter less than the first diameter can access both the first septum and the second septum, while the first needle exhibiting the first diameter can access the first septum but not the second septum.

2. The therapeutic fluid delivery system of claim 1, wherein the inlet port is configured so the second fluid delivery needle penetrates the first septum before the second fluid delivery needle penetrates the second septum.

3. The therapeutic fluid delivery system of claim 1, wherein the inlet port defines a fluid intake aperture interposed between the first septum and the second septum.

4. The therapeutic fluid delivery system of claim 1, further comprising the first fluid delivery needle and the second fluid delivery needle.

5. The therapeutic fluid delivery system of claim 1, wherein at least one of the first reservoir or the second reservoir is defined by a bellows.

6. The therapeutic fluid delivery system of claim 5, wherein the bellows comprises a convolution constructed of an elastomer.

7. The therapeutic fluid delivery system of claim 1, further comprising a propellant reservoir.

8. The therapeutic fluid delivery system of claim 1, further comprising one or more sensors configured to detect when the second fluid delivery needle penetrates the first septum but not the second septum, and further detect when the second fluid delivery needle penetrates both the first septum and the second septum;
wherein, to detect when the second fluid delivery needle penetrates the first septum but not the second septum, and further detect when the second fluid delivery needle penetrates both the first septum and the second septum, the one or more sensors are configured to detect a characteristic that varies when the second fluid delivery needle penetrates the first septum but not the second septum, and further varies when the second fluid delivery needle penetrates both the first septum and the second septum, the system further comprising:
a processor configured to determine that the second fluid delivery needle has penetrated the first septum but not the second septum based on the detected characteristic.

9. The therapeutic fluid delivery system of claim 8, wherein the processor is configured to determine that the second fluid delivery needle has penetrated both the first septum and the second septum based on the detected characteristic.

10. The therapeutic fluid delivery system of claim 8, wherein the characteristic is selected from the group consisting of pressure, current, voltage, and resistance.

11. The therapeutic fluid delivery system of claim 10, wherein the characteristic is pressure, the one or more sensors comprise a first pressure sensor and a second pressure sensor, and the processor is configured to determine that the second fluid delivery needle has penetrated the first septum but not the second septum based on the pressure detected by the first pressure sensor, and further that the second fluid delivery needle has penetrated both the first septum and the second septum based on the pressure detected by the second pressure sensor.

12. The therapeutic fluid delivery system of claim 10, wherein the characteristic is electrical resistance.

13. The therapeutic fluid delivery system of claim 12, further comprising a wire mesh proximate to at least one of the first septum or the second septum, wherein the wire mesh is electrically connected to the one or more sensors.

14. The therapeutic fluid delivery system of claim 13, wherein the wire mesh comprises a first wire mesh proximate to the first septum, and further comprising a second wire mesh proximate to the second septum.

15. The therapeutic fluid delivery system of claim 12, further comprising a set of two or more stacked discs proximate to at least one of the first septum or the second septum, wherein each of the discs comprises a plurality of slots, wherein the slots in the respective discs are arranged at an angle to one another to form a plurality of apertures in the set of stacked discs, and wherein the set of stacked discs is electrically connected to the one or more sensors.

16. The therapeutic fluid delivery system of claim 15, wherein the angle between the slots of the respective discs of the set of stacked discs is at least one of approximately 90 or approximately 120 degrees.

17. The therapeutic fluid delivery system of claim 15, wherein the set of stacked discs comprises a first set of stacked discs proximate to the first septum, and further comprising a second set of stacked discs proximate to the second septum.

18. The therapeutic fluid delivery system of claim 8, further comprising a programmer, wherein the processor is configured to cause the programmer to at least one of vibrate, issue an audible sound, display text, or display a visual graphic when at least one of the first septum but not the second septum is penetrated by the second fluid delivery needle or when both the first septum and the second septum are penetrated by the second fluid delivery needle.

19. The therapeutic fluid delivery system of claim 18, wherein the processor is configured to cause the programmer to at least one of vibrate, issue an audible sound, display text, or display a visual graphic when at least one of the first fluid delivery needle and the second fluid delivery needle is withdrawn from at least one of the first septum or the second septum.

20. The therapeutic fluid delivery system of claim 1, further comprising a valve interposed between a fluid delivery pump and the first and second reservoirs.

21. The therapeutic fluid delivery system of claim 20, wherein the valve comprises a rotary valve.

22. The therapeutic fluid delivery system of claim 20, wherein the valve comprises a first valve interposed between the first reservoir and the fluid delivery pump, and a second valve interposed between the second reservoir and the fluid delivery pump.

23. The therapeutic fluid delivery system of claim 22, wherein the first valve is configured to actuate in response to instructions from a processor, and the second valve is a passive valve.

24. The therapeutic fluid delivery system of claim 23, wherein the second valve is a check valve.

25. The therapeutic fluid delivery system of claim 24, wherein a force required to open the check valve is less than or equal to approximately 2 pounds per square inch.

26. The therapeutic fluid delivery system of claim 23, wherein the first valve includes a solenoid.

27. The therapeutic fluid delivery system of claim 1, wherein the inlet port that exhibits the reduced cross-sectional area between the first septum and the second septum comprises an insert that reduces the cross-sectional area between the first septum and the second septum.

28. The therapeutic fluid delivery system of claim 1, wherein the inlet port that exhibits the reduced cross-sectional area between the first septum and the second septum comprises a conical section that reduces the cross-sectional area between the first septum and the second septum.

29. The therapeutic fluid delivery system of claim 1, wherein the inlet port defines an aperture between the first septum and the second septum such that the inlet port permits the second needle exhibiting the second diameter less than the first diameter to access both the first septum and the second septum, and the inlet port permits the first needle exhibiting the first diameter to access the first septum but prevents the first needle exhibiting the first diameter from accessing the second septum.

30. A method comprising:
  inserting a first fluid delivery needle having a first diameter into an inlet port of a fluid delivery device, wherein the inlet port is configured to receive the first fluid delivery needle;
  inserting a second fluid delivery needle having a second diameter less than the second diameter into the inlet port of the fluid delivery device, wherein the inlet port is further configured to receive the second fluid delivery needle;
  wherein the inlet port comprises a first septum and a second septum, the inlet port is configured for fluid communication between the first fluid delivery needle and a first reservoir when the first fluid delivery needle penetrates the first septum but not the second septum, and the first reservoir is configured to house a first therapeutic fluid; and
  wherein the inlet port is further configured for fluid communication between the second fluid delivery needle and a second reservoir when the second fluid delivery needle penetrates both the first septum and the second septum, wherein the second reservoir is configured to house a second therapeutic fluid; and
  wherein the inlet port exhibits a reduced cross-sectional area between the first septum and the second septum such that the second needle exhibiting the second diameter less than the first diameter can access both the first septum and the second septum, while the first needle exhibiting the first diameter can access the first septum but not the second septum.

31. The method of claim 30, further comprising detecting, by one or more sensors, when the second fluid delivery needle penetrates the first septum but not the second septum and further when the second fluid needle penetrates both the first septum and the second septum;
   wherein detecting when the second fluid delivery needle penetrates the first septum but not the second septum and further when the second fluid needle penetrates both the first septum and second septum comprises:
      detecting a characteristic that varies when the second fluid delivery needle penetrates the first septum but not the second septum or both the first septum and the second septum; and
      determining, by a processor, that the second fluid delivery needle has penetrated the first septum but not the second septum based on the detected characteristic.

32. The method of claim 31, wherein determining that the second fluid delivery needle has penetrated the first septum but not the second septum or both the first septum and the second septum comprises determining that the second fluid delivery needle has penetrated both the first septum and the second septum based on the detected characteristic.

33. The method of claim 31, wherein the characteristic is selected from the group consisting of pressure, current, voltage, and resistance.

34. The method of claim 31, further comprising generating a needle penetration indication when the first septum but not the second septum is penetrated by the second fluid delivery needle or when both the first septum and the second septum are penetrated by the second fluid delivery needle, wherein generating the needle penetration indication comprises at least one of vibrating, issuing an audible sound, displaying text, or displaying a visual graphic.

35. The method of claim 31, further comprising generating a needle withdrawal indication when at least one of the first fluid delivery needle and the second fluid delivery needle is withdrawn from at least one of the first septum or the second septum, wherein generating the needle withdrawal indication comprises at least one of vibrating, issuing an audible sound, displaying text, or displaying a visual graphic.

36. A method comprising:
   inserting a first fluid delivery needle having a first diameter into an inlet port of a fluid delivery device to a first depth sufficient to penetrate a first septum of the inlet port but not a second septum of the inlet port to selectively access a first reservoir;
   inserting a second fluid delivery needle having a second diameter less than the second diameter into the inlet port of the fluid delivery device to a second depth greater than the first depth to penetrate both the first septum and the second septum to selectively access a second reservoir different from the first reservoir;
   delivering fluid from the first fluid delivery needle to the first reservoir when the first fluid delivery needle penetrates the first septum but not the second septum; and
   delivering fluid from the second fluid delivery needle to the second reservoir when the second fluid delivery needle penetrates both the first septum and the second septum;
   wherein the inlet port exhibits a reduced cross-sectional area between the first septum and the second septum such that the second needle exhibiting the second diameter less than the first diameter can access both the first septum and the second septum, while the first needle exhibiting the first diameter can access the first septum but not the second septum.

37. The method of claim 36, further comprising:
   detecting, by one or more sensors, a characteristic that varies when the second fluid delivery needle penetrates the first septum but not the second septum or both the first septum and the second septum.

38. A fluid delivery system comprising:
   first means for housing a first therapeutic fluid;
   second means for housing a second therapeutic fluid;
   means for receiving a first fluid delivery needle having a first diameter and a second fluid delivery needle having a second diameter less than the first diameter, wherein the means for receiving the first fluid delivery needle and the second fluid delivery needle comprises a first septum and a second septum, and
   wherein the first means for housing the first therapeutic fluid is in fluid communication with the first fluid delivery needle when the first fluid delivery needle penetrates the first septum but not the second septum, and wherein the second means for housing the second therapeutic fluid is in fluid communication with the second fluid delivery needle when the second fluid delivery needle penetrates both the first septum and the second septum; and
   wherein the means for receiving the first fluid delivery needle and the second delivery needle exhibits a reduced cross-sectional area between the first means for housing the first therapeutic fluid and the second means for housing the second therapeutic fluid such that the second needle exhibiting the second diameter less than the first diameter can access both the first means for housing the first therapeutic fluid and the second means for housing the second therapeutic fluid, while the first needle exhibiting the first diameter can access the first means for housing the first therapeutic fluid but not the second means for housing the second therapeutic fluid.

39. The fluid delivery system of claim 38, further comprising means for detecting when the second fluid delivery needle penetrates the first septum but not the second septum, and further when the second fluid delivery needle penetrates both the first septum and the second septum;
   wherein the means for detecting detects a characteristic that varies when the second fluid delivery needle penetrates the first septum but not the second septum, and further when the second fluid delivery needle penetrates both the first septum and the second septum, wherein the characteristic is selected from the group consisting of pressure, current, voltage, and resistance, and wherein the fluid delivery system further comprises means for determining that the second fluid delivery needle has penetrated the first septum but not the second septum based on the detected characteristic and further that the second fluid delivery needle has penetrated both the first septum and the second septum based on the detected characteristic.

* * * * *